(12) United States Patent
Lee et al.

(10) Patent No.: US 11,458,120 B2
(45) Date of Patent: Oct. 4, 2022

(54) APTAMER-DRUG CONJUGATE AND USE THEREOF

(71) Applicant: INTEROLIGO CORPORATION, Gyeonggi-do (KR)

(72) Inventors: Jung Hwan Lee, Gyeonggi-do (KR); Jong Hun Im, Seoul (KR); Jong In Kim, Seoul (KR)

(73) Assignee: INTEROLIGO CORPORATION, Gyeonggi-Do (KR)

( * ) Notice: Subject to any disclaimer, the term of this patent is extended or adjusted under 35 U.S.C. 154(b) by 0 days.

(21) Appl. No.: 16/473,771

(22) PCT Filed: Dec. 4, 2017

(86) PCT No.: PCT/KR2017/014060
§ 371 (c)(1),
(2) Date: Jun. 26, 2019

(87) PCT Pub. No.: WO2018/124512
PCT Pub. Date: Jul. 5, 2018

(65) Prior Publication Data
US 2019/0358202 A1    Nov. 28, 2019

(30) Foreign Application Priority Data
Dec. 26, 2016  (KR) ........................ 10-2016-0179111

(51) Int. Cl.
| A61K 31/4025 | (2006.01) |
| A61K 31/535 | (2006.01) |
| A61K 31/4745 | (2006.01) |
| A61K 47/10 | (2017.01) |
| A61K 47/54 | (2017.01) |
| C12N 15/115 | (2010.01) |

(52) U.S. Cl.
CPC .......... *A61K 31/4025* (2013.01); *A61K 47/10* (2013.01); *A61K 47/54* (2017.08); *C12N 15/115* (2013.01)

(58) Field of Classification Search
CPC ............ A61K 31/4025; A61K 48/0058; A61K 31/535; A61K 31/4745; A61K 47/10; A61K 47/54
See application file for complete search history.

(56) References Cited

U.S. PATENT DOCUMENTS

| 2014/0213636 A1 | 7/2014 | Lee et al. |
| 2016/0130357 A1 | 5/2016 | Mukherjee |

FOREIGN PATENT DOCUMENTS

| WO | WO 84/03285 A1 | 8/1984 |
| WO | WO 00/32237 A1 | 6/2000 |
| WO | WO-2004010957 | * 5/2004 |
| WO | WO 2004/073656 A2 | 9/2004 |
| WO | WO 2012/149198 A2 | 11/2012 |
| WO | WO 2015/184224 A1 | 12/2015 |
| WO | WO 2016/004043 A1 | 1/2016 |

OTHER PUBLICATIONS

Thiviyanathan et al. ("Aptamers and the Next Generation of Diagnostic Reagents." Proteomics Clin Appl. Dec. 2012; 6(0): 563-573). (Year: 2012).*
Notice of Allowance dated Aug. 21, 2019 from Korean Patent Office in a counterpart Korean Patent Application No. 10-2016-0179111 (all the cited references are listed in this IDS.) (Translation is submitted herewith.).
Hongwen Li et al., "An anti-HER2 antibody conjugated with monomethyl auristatin E is highly effective in HER2-positive human gastric cancer", Cancer Biology & Therapy vol. 17, No. 4, pp. 346-354, 2016.
International Search Report for PCT/KR2017/014060 dated May 31, 2018.
Zhou, J. et al., "Cell-type-specific, Aptamer-functionalized Agents for Targeted DiseaseTherapy", Molecular Therapy-Nucleic Acids, vol. 3, e169, pp. 1-17, 2014.
Li, L. et al.. "Nucleolin-targeting Liposomes Guided by Aptamer AS 1411 for the Delivery of siRNA for the Treatment of Malignant Melanomas", Biomaterials, vol. 35, pp. 3840-3850, 2014.
Zhu, G. et al., "Aptamer-drug Conjugates", Bioconjugate Chemistry, vol. 26. No. 11, pp. 2186-2197, 2015.
Sun, H. et al., "Oligonucleotide Aptamers: New Tools for Targeted Cancer Therapy", Molecular Therapy-Nucleic Acids, vol. 3, e 182, pp. 1-14, 2014.
Jiang, F. et al., "Progress and Challenges in Developing Aptamer-functionalized Targeted Drug Delivery Systems", International Journal of Molecular Sciences, vol. 16, pp. 23784-23822, 2015.
Office action dated Aug. 31, 2021 from Japan Intellectual Property Office in a counterpart Japanese Patent Application No. 2019-555545 (all the cited references are listed in this IDS.) (English translation is also submitted herewith.).
Kyue Yim Lee et al., "Bioimaging of Nucleolin Aptamer-Containing 5-(N-benzylcarboxyamide)-2'-deoxyuridine More Capable of Specific Binding to Targets in Cancer Cells", Hindawi Publishing Corporation Journal of Biomedicine and Biotechnology, 2010,vol. 2010, Article ID 168306, 9 pages, Hindawi Publishing Corporation.
European Search Report for EP17887935.9 dated Jul. 28, 2020 from European patent office in a counterpart European patent application.
Thu Le Trinh et al., "A Synthetic Aptamer-Drug Adduct for Targeted Liver Cancer Therapy", PLOS ONE , vol. 10(11), 2015.

(Continued)

*Primary Examiner* — Jeffrey S Lundgren
*Assistant Examiner* — Chris E Simmons
(74) *Attorney, Agent, or Firm* — The PL Law Group, PLLC

(57) ABSTRACT

A cancer targeted therapeutic agent includes a drug-linker-AS1411 structure. The drug may be selected from monomethyl auristatin E (MMAE), monomethyl auristatin F (MMAF), cytarabine, gemcitabine, maytansine, DM1, DM4, calicheamicin and a derivative thereof, doxorubicin, duocarmycin and a derivative thereof, pyrrolobenzodiazepine (PBD), SN-38, a-amanitin, or a tubulysin analog.

4 Claims, 16 Drawing Sheets

Specification includes a Sequence Listing.

(56) References Cited

OTHER PUBLICATIONS

Jonathan W et al., "Aptamer-Mediated Delivery of Splice-Switching Oligonucleotides to the Nuclei of Cancer Cells", Nucleic Acid Therapeutics, vol. 22(3), No. 3, 2012.
Feng Jiang et al., "Progress and Challenges in Developing Aptamer-Functionalized Targeted Drug Delivery Systems", Int. J. Mol. Sci. vol. 16(10), 2015.

\* cited by examiner

Tumor size at day 30 after treatment

APTAMER-DRUG CONJUGATE AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/014060 filed on Dec. 4, 2017, which claims priority to the benefit of Korean Patent Application No. 10-2016-0179111 filed in the Korean Intellectual Property Office on Dec. 26, 2016, the entire contents of which are incorporated herein by reference.

TECHNICAL FIELD

The present invention relates to an [anti-nucleolin GRO aptamer]-Toxin conjugate for treatment of targeted cancer and a synthetic method thereof, and more particularly, to an [anti-nucleolin aptamer]-Toxin conjugate with verified in vitro/vivo efficacy, thereby exhibiting excellent effects in treatment of cancer, as well as use thereof.

BACKGROUND ART

Until now, numerous therapeutic agents including anticancer drugs have been developed and proposed as medicines through clinical trials. However, how to choose and effectively deliver some materials having desired therapeutic effects such as targeted anticancer drugs to the desired site of onset are still new fields to be researched. Anticancer drugs are generally used with approximately maximum tolerated dose in order to afford clinical effects, and such anticancer drugs kill rapidly proliferating cells, but cannot distinguish tumor cells or tumor tissues from normal cells. Chemotherapy as described above has a drawback that therapeutic index and therapeutic window of the anticancer drugs are considerably low due to non-tumor specific systemic toxicity and cytotoxicity. Further, since the chemotherapy may cause anticancer drug-resistance in long-term therapy, there is an urgent need for new and improved therapies to kill cancer cells by accurately delivering a cytotoxic drug to only cancer cells.

Over the last 30 years, a number of attempts to effectively deliver a drug to a target thus to increase efficacy have been made. In this regard, it is believed that an attempt for clinical trials of antibody-drug conjugates (ADC), which is a combination of an antibody and a drug, has high probability of success, as compared to existing naked antibodies. In recent years, ADC has successfully finished a Phase 3 clinical trial by Scattle Genetics Inc. and Imunog Co., received FDA approval and released on the market, and therefore, it can be said to open a new chapter in therapeutic agents. However, an antibody is usually composed of a large protein and entails many problems in quality control (QC), in particular, in regard to drug attached positions, the number of attached drugs (1 to 6, average 3.5), positions for attachment, etc. Target-oriented properties of an aptamer which is comparable to an antibody, as well as development of aptamer-dug conjugate consisting of the aptamer and a therapeutic agent have attained advantages, wherein chemical reactions thereof can be easily performed, and therefore, the number of therapeutic agents and drug attached positions can be desirably adjusted. Accordingly, it is believed that applying superiority of aptamers over antibodies may increase possibility of success.

Aptamer-drug conjugates (ApDCs) are highly toxic, and it is predicted that therapeutic effects may be maximized without side effects by attaching a target-oriented aptamer to the drug, which was difficult in actually clinical use, and accurately delivering the conjugate to only cancer cells.

In fact, as a result of assessing the conventional ADC technology (Antibody-Drug Conjugate Technology) developed up to now, it could be understood that combining the antibody with the drug entails technical difficulties as well as disadvantages. Using an aptamer enabled easier and more efficient development of aptamer-combined therapeutic agents, which in turn are intended to be applied to medical treatment as a targeted anticancer drug.

ADC Technology (Antibody-Drug Conjugate Technology)

ADC technology is specifically focused on a drug that targets only cancer cells by maximally utilizing advantages of an antibody (specificity, non-toxicity in circulation and pharmacokinetics). ADC consists of three components including a monoclonal antibody, a drug and a linker connecting the monoclonal antibody and the drug, and ADC technology is a method for delivering the drug to tumor cells by using the antibody specifically binding to a specific antigen expressed on surfaces of the cancer cells.

ADC generally enters a cell when the antibody specifically binding to a target is bound to the target. ADC moved into the cell is separated from the target, is fused with other vesicles in the cell and then proceeds to a following endosome-lysosome path. Then, the linker is cut by proteases under an acidic environment of endosomes, and the activated "free" drug moves to cytoplasm by passing through a lysosomal membrane, and then is bound to a molecular target of the drug, so as to stop a cell cycle of the tumor cells and kill the same due to apoptosis. A desired amount of drug may be passively diffused, actively transported or discharged to an outside of the cells through dead cells. Herein, when the discharged drug may enter surrounding cells during passing through a permeable cell membrane, causing so-called 'by-stander cell killing' phenomenon and side effects on a patient.

Difficulties (QC) in ADC Development

Development of the ADC (antibody-drug conjugate) has started from the 1980s and still has difficulties in QC during an ADC synthesis process in addition to the development of a stable linker for clinical practice in application of clinical trials. In other words, when binding DM1 (drug) to an antibody (huJ591), if a mixture of a single antibody (huj591) conjugated with 1 to 7 DM1 drugs is acquired, these drugs cannot be separated/purified. Therefore, ADC conjugated with average 3.5 DM1 drugs is usually used in clinical trials.

Further, the antibody (Tmab) has 88 lysines to which the drugs (DM1) are attached. It is not easy to identify which one among 88 lysines has a conjugation site, at which the average 3.5 drugs (DM1) are attached. That is, in order to determine a conjugation site, trypsin digestion and Asp-N protease digestion are performed, and the resulting fragments are analyzed through ESI-TOFMS. Comparing the analyzed results may generally determine the conjugation site of the drugs (DM1).

Further, with respect to ADC production, it is difficult to manage QC since an average constitutional composition of a drug attached to an antibody is altered according to every production batch. In other words, in a case of attaching DOTA to an antibody (juJ591), MALDI-TOF MS spectra show that 5.0 DOTAs are attached to the antibody in batch A while 8.9 DOTAs are attached to the antibody in batch B. In other batches, 6.0 and 6.2 DOTAs are attached thereto. As described above, ADC (antibody-drug conjugate) synthesis involves many problems to be solved such as difficulties in exact QC due to characteristics of the antibody itself during drug combination, and now is under study with efforts to solve such problems in the ADC process.

Limitations of ADC (Antibody-Drug Conjugate):

Treatment effects using a drug may be achieved by delivering the drug, to which an antibody is bound in a target-oriented manner, to cancer cells. However, the drug, which is bound to the antibody and reaches the cancer cells, is only 2% or less, thus causing a problem of very low efficiency. Since a stable anticancer drug with clinical approval such as doxorubicin is stable but has low efficacy, highly toxic agents having toxicity of 100 to 1000 times that of doxorubicin are typically adopted as a drug for binding to the antibody in order to solve the above problem.

Aptamer

An aptamer is a DNA or RNA oligonucleotide useable for diagnosis or targeted therapy, which has similar properties to an antibody, and is highly selectively combined with a biomark causing diseases such as cancer. That is, the aptamer has unique 3-dimensional structures depending upon target materials, wherein the 3-dimensional structure is very selectively and strongly bound to a marker protein (cancer inducing protein, biomark), and therefore, may be a new bio-capturing material enabling target treatment, personalized diagnostic therapy or missile therapy.

Comparison Between Aptamer and Antibody

As most successful antibodies as a targeted therapeutic agent, 30 species of antibody targeted therapeutic agents currently have received FDA approval and are commercially available, while about 300 species are under a clinical trial phase. However, development costs are too expensive and these agents have already reached saturation. Therefore, advanced pharmaceutical companies are being converted into development of novel therapeutic agents.

An antibody consists of a protein and still has difficulties such as creation in vivo, but an aptamer can discover a lead compound in vitro more quickly than the antibody and can be easily synthesized and modified, thereby being expected as a new bio-capturing reagent referred to as a "chemical antibody".

Aptamer Therapeutic Agent Development Trends

Eyetech Inc. received FDA approval in 2006 with the originally first aptamer therapeutic agent 'Macugen,' which started to come to the market by the Pfizer licensing. Macugen is a therapeutic agent to treat age-related macular degeneration (AMD) as a cause of macular degeneration of blindness due to presbyopia, which exhibits therapeutic effects of inhibiting a vascular endothelial growth factor (VEGF) that causes the growth of abnormal blood vessels. After that, with increased possibilities of aptamer therapeutic agents, other manufacturers such as Merck Serono, Takeda, Pfizer, Elan, Eli Lilly, GlaxoSmithKline, Ribomic, etc. have taken part in the development of new aptamer pharmaceuticals, resulting in about 10 species of aptamers that are currently in a clinical phase.

The aptamer is often called a "chemical antibody" since having higher target binding affinity and selectivity, as compared to the antibody. Further, compared to a biological antibody, the aptamer is produced by chemical synthesis and thus may be more effective in drug attachment, as well as have an advantage of very simple QC. If the aptamer solves a problem of the antibody, that is, low target reaching rate, it is predicted that low efficiency of the existing ADCs (antibody-drug conjugates) can be overcome.

An aptamer-Drug conjugate is also expected to have possibility as a new therapeutic agent area, however, researches for development of a therapeutic agent using the same is still at an early stage. Recently, Weihong Tang group at the University of Florida has prepared an aptamer-drug conjugate (Sgc8c-Dox conjugate) by combining a doxorubicin (Dox) anticancer drug to an aptamer (Sgc8c), and then compared to doxorubicin in terms of anticancer effects, however, there was no significant difference. Since it was difficult to separate/purify the same from a naked aptamer, that is, Sgc8c, during Sgc8c-Dox conjugate synthesis, high purity Sgc8c-Dox conjugate cannot be acquired and both the Sgc8c-Dox conjugate and doxorubicin exhibit similar cytotoxic effects (20%).

GRO Aptamer

Paula J. Bate professor of the University of Louisville has first synthesized GRO (Guanine-Rich Oligonucleotide) aptamer in 1990 and disclosed a mechanism of the same specifically binding to a nucleolin protein which is highly expressed in cancer patients, and therefore, proposing possibility for development of novel anticancer therapeutic agent. At present, one of GRO aptamers is under development as AS1411 code, which is a therapeutic agent of renal and non-small cell carcinoma (AML), by Antisoma (UK). Further, with respect to AML, a Phase II clinical trial has recently been completed.

Typically, the aptamer is very unstable inside a body and, in order to increase nuclease residence or a circulation in vivo, an aptamer formulation (PEG-aptamer-idT) prepared by PEGylation of idT (invert dT) at 3' position to 5' position is used in clinical trials.

GRO aptamer has a unique structure of G-quardruplex and thus is very stable and specifically bound to nucleolin which is highly expressed in cancer cells. That is, the GRO aptamer may interfere molecular interactions and functions of nucleolin in nucleus, cytoplasma and membranes, and thus inhibits expression of nucleolin so as to have antiproliferative effects and promote expression of p53 as a tumor suppressor protein, thereby inducing necrosis of cancer cells.

At present, AS1411 is GRO aptamer having completed Phase II clinical trials and on the launch of Phase III clinical trials with respect to non-small carcinoma and renal carcinoma by Antisoma (UK). This is a very stable aptamer specifically binding to nucleolin expressed in almost of all cancers and thus has anticancer effects to a variety of cancers.

Problems and prospects of existing studies: AS1411 currently under development as an anti-nucleolin aptamer drug by Antisoma (UK) is GRO DNA aptamer having ggtggtggtggttgtggtggtggtgg (SEQ ID NO: 1) sequence, which has currently completed Phase II clinical trials as a therapeutic agent for renal cancer and non-small cell lung cancer. However, due to uncertainty in efficacy validation, Antisoma (UK) did not proceed further Phase III clinical trials for non-small carcinoma, but transferred the same to Advanced Cancer Therapeutics Inc. This company is now preparing Phase III clinical trials of ACT-GRO-777 (renamed AS1411).

Oligonucleotide drugs including GRO aptamer currently developed and being used in clinical trials are very rapidly decomposed in vivo by nuclease enzymes present in large quantities in the blood plasma. In particular, an injection type therapeutic agent is known to be more quickly degraded if not processed by any chemically stable method. In order to regulate a degradation rate of the therapeutic agent, oligonucleotides may be chemically modified or a complex of oligonucleotide combined with any suitable carrier may be formed, thus reducing a degradation rate thereof. A variety of chemical modifications including, for example, substitution of ribose 2'-OH group resistant to nuclease with 2'F or 2'OMe group, alteration of a phosphor backbone from PO to PS, etc. have been successfully used in applications such as antisense or siRNA. The first aptamer therapeutic agent, Macugen, having received PDA permission in 2004 and now being commercially available in the market was also under optimization after discovery of aptamer.

GRO aptamer also needs nucleolin targeting specificity which is very important in improving therapeutic effects. Further, "Off-target effects" deteriorating therapeutic efficacy caused if the aptamer is combined with different proteins other than the nucleolin protein should be minimized. The reason why Antisoma (UK) could not easily enter Phase III clinical trials of AS1411 as the first GRO aptamer therapeutic agent after completion of Phase II clinical trials for non-small carcinoma (AML) is presumed not because of side effects or toxicity but due to a disadvantage that a great dosage is administered while not attaining optimum anticancer effects.

SUMMARY

Accordingly, the present inventors have synthesized an AS1411-drug conjugate by successful conjugation of a drug to AS1411, and found that the AS1411-drug conjugate has a targeting ability of AS1411 to nucleolin over-expressed in cancer cells and is more effective in cancer targeted treatment in vitro and in vivo, as compared to using the drug delivered and attached to the only cancer cells.

A cancer targeted therapeutic agent of the present invention has the following drug (R)-linker (L)-AS1411 structure.

(SEQ ID NO: 1)
R-L-ggtggtggtggttgtggtggtggtgg

Drug-linker-AS1411 Conjugate
[R-L-AS1411]

A position at which the drug is linked, is particularly preferably 12 and 13 positions or 12 or 13 position.

(SEQ ID NO: 9)

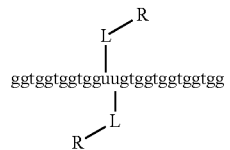

12,13-[Drug]₂-linker-AS1411
Conjugate 12,13-[R-L]₂-AS1411

(SEQ ID NO: 9)

ggtggtggtgguugtggtggtggtgg 12 or 13-[Drug]₂-linker-AS1411
Conjugate 12 or 13-[R-L]₂-AS1411

Herein, the drug R used herein is preferably monomethyl auristatin E (MMAE), monomethyl auristatin F (MMAF), cytarabine, gemcitabine, maytansine, DM1, DM4, calicheamicin and derivatives thereof, doxorubicin, duocarmycin and derivatives thereof, pyrrolo-benzodiazepine (PBD), SN-38, α-ammantin, tubulysin analong, etc.

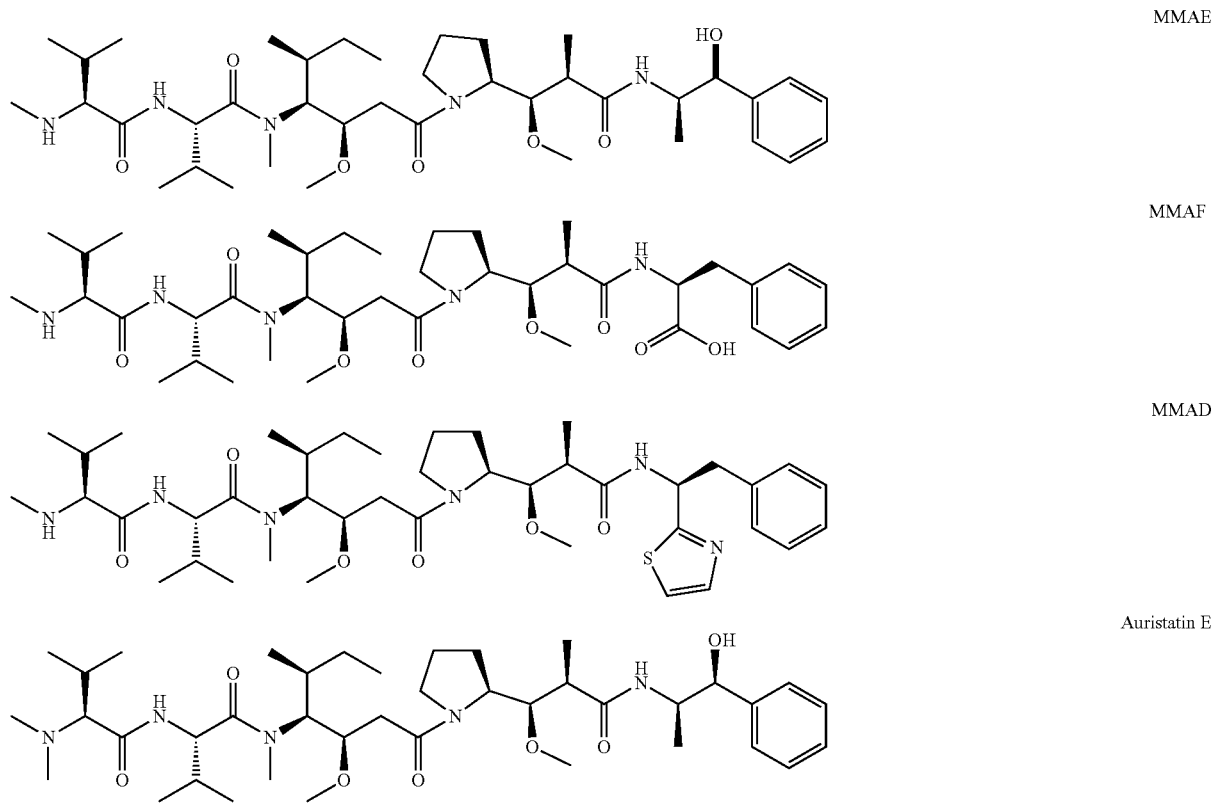

MMAE

MMAF

MMAD

Auristatin E

Auristatin F
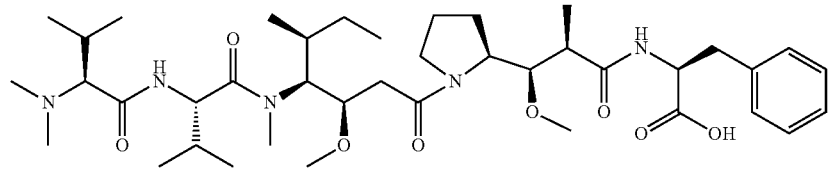
DM1      DM4
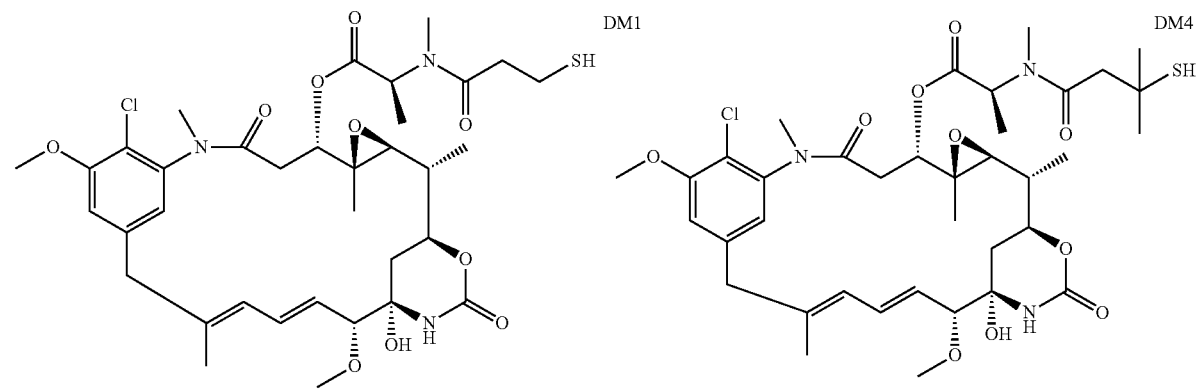
Nemorubicin      PNU-159682
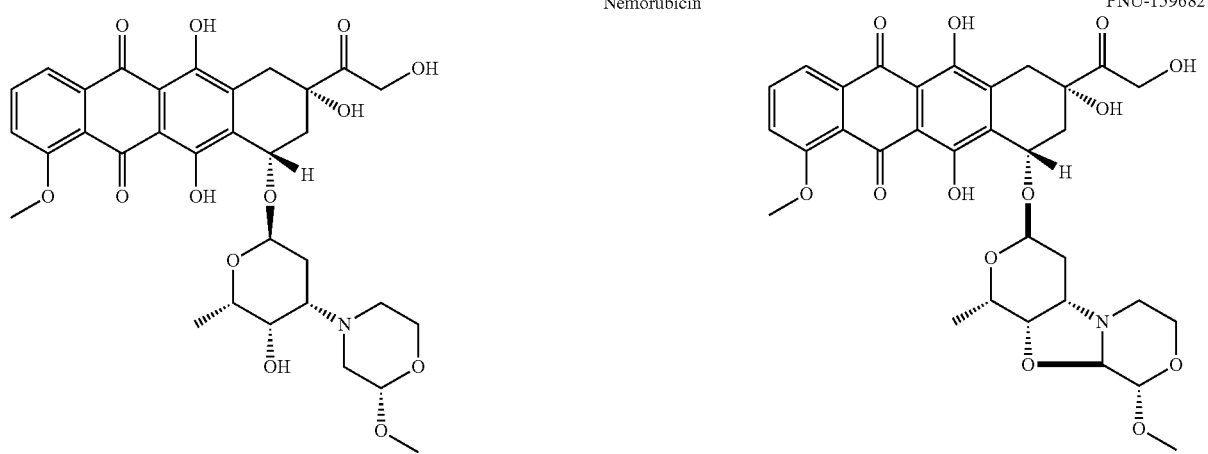
Tubulysin M
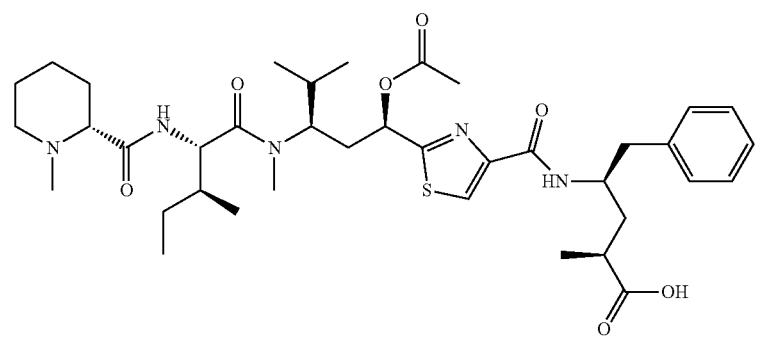

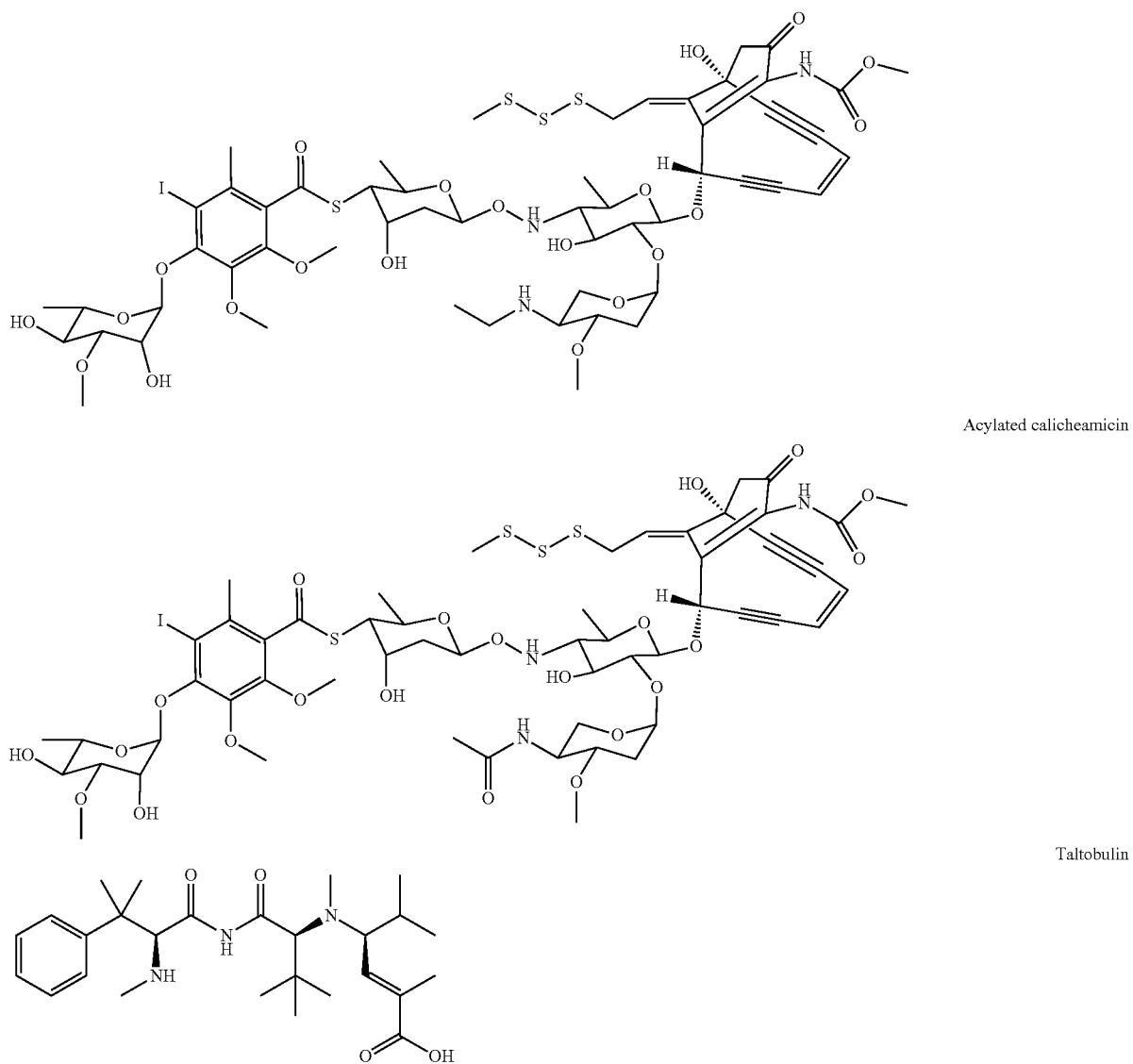

wherein L consists of X-Y [R-Y-X-AS1411],

Y may be selected from the group consisting of maleimidocaproyl-valine-citrulline-p-aminobenzoyloxycarbonyl (MC-Val-Cit-PAB), hydrazone, peptide, disulfide, thioether, valine-citrulline, N-maleimidomethyl cyclohexane-1-carboxylate (MCC), maleimidocaproyl, mercaptoacetamidocaproly, N-succinimidyl 4-(2-pyridyldithio)pentanoate (SPP), SMCC, succinimidyl 4-(N-maleimidomethyl)cyclohexane-1-carboxylate (SMCC), N-succinimidyl 4-(2-pyridylthio)pentanoate (SPDB), phosphodiester bond and nucleotides, and X may be selected from the group consisting of 5'-thiol-modifier C6, thiol-modifier C6 S—S, dithiolserinol, PC amino-modifier, 5'-amino-modifier C3, 5'-amino-modifier C6, 5'-amino-modifier C12, 5'-amino-modifier TEG, amino-modifier C2 dT, amino-modifier C6 dT, S-Bz-thiol-modifier C6-dT, phosphodiester bond and nucleotide.

AS1411-drug conjugate of the present invention is more effective in cancer targeted treatment in vitro and in vivo than the case of using the drug alone.

DETAILED DESCRIPTION

Hereinafter, the present invention will be described in more detail with reference to the following embodiments.

[GRO Aptamer]-Drug Conjugate Synthesis

Example 1

Synthesis of MMAE-(PAB-Cit-Val-MC-S-C6)-$T_3$-AS1411 [AS1411-MMAE conjugate]

By reacting maleimidocaproyl-valine-citrulline-p-aminobenzoyloxycarbonylmonomethyl auristatin E [MC-Val-Cit-PAB-MMAE] with HS-C6-tttggtggtggtggttgtggtggtggtgg (SEQ ID NO: 2) [HS-C6-$T_3$-AS1411], monomethyl auristatin E-p-aminobenzoyloxycarbonyl-citrulline-valine-Mal-S-C6-tttggtggtggtggttgtggtggtggtgg (SEQ ID NO: 2) [MMAE-(PAB-Cit-Val-MC-S-C6)-$T_3$-AS1411] was synthesized. In other words, RSS-C6-tttggtggtggtggttgtggtggtggtgg (SEQ ID NO: 2) [RSS-C6-$T_3$-AS1411] was subjected to reductive reaction in the presence of DTT for about 3 hours, and the remaining DTT was removed by a centrifuge and replaced with an SB17 buffer solution, resulting in HS-C6-tttggtggtggtggttgtggtggtggtgg (SEQ ID NO: 2) [HS-C6-$T_3$-AS1411]. After putting MC-Val-Cit-PAB-MMAE dissolved in a small amount of DMSO into the resultant product, the mixture was shaken overnight. Separation/purification were performed through reverse phase HPLC (Waters-Xbridge OST C18 10×50 mm, 65, TEAE/CAN buffer).

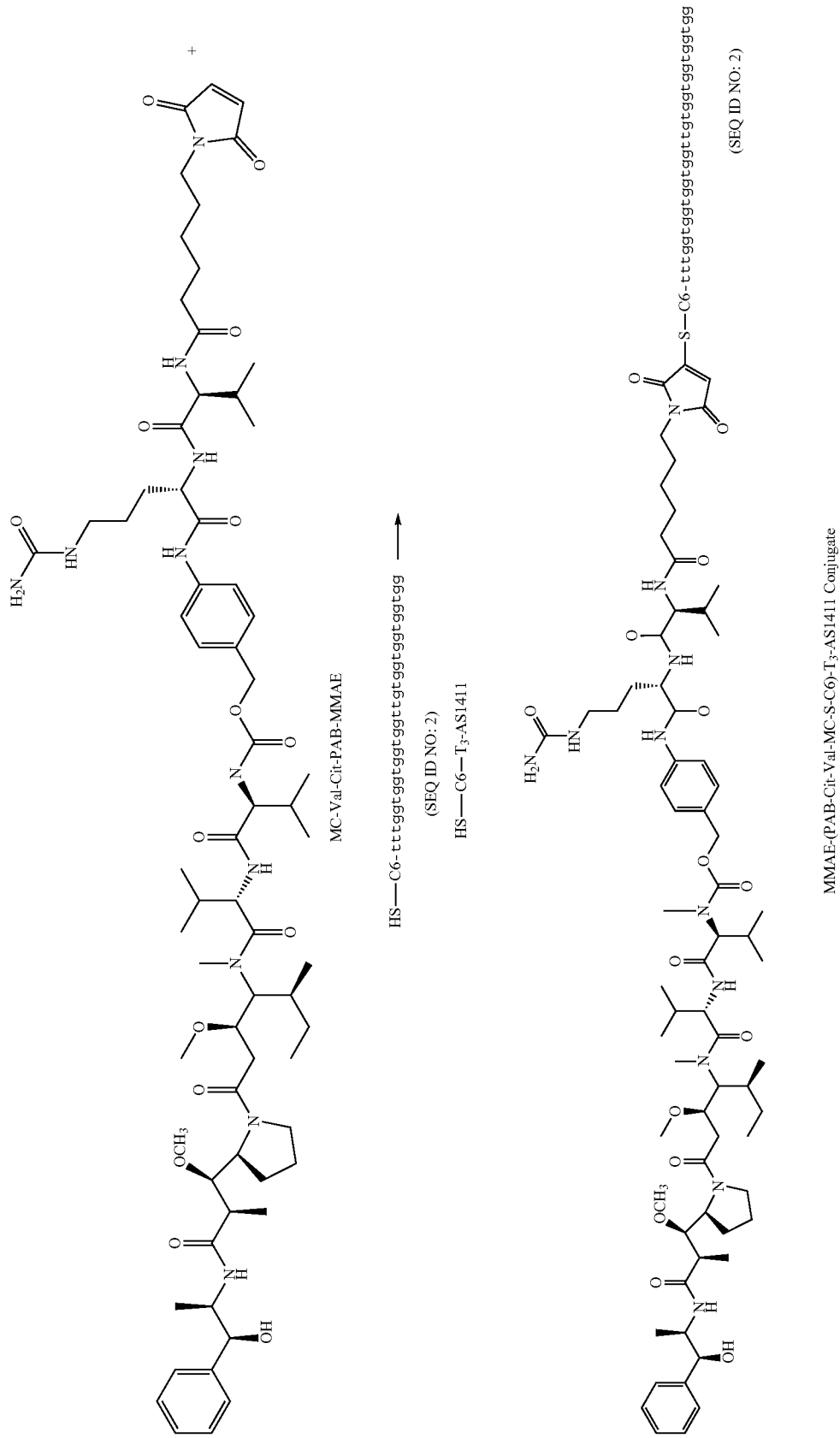

MMAE-(PAB-Cit-Val-MC-S-C6)-T$_3$-AS1411 was synthesized by reaction of MC-Val-Cit-PAB-MMAE and HS-06-T$_3$-AS1411

Figure 1:
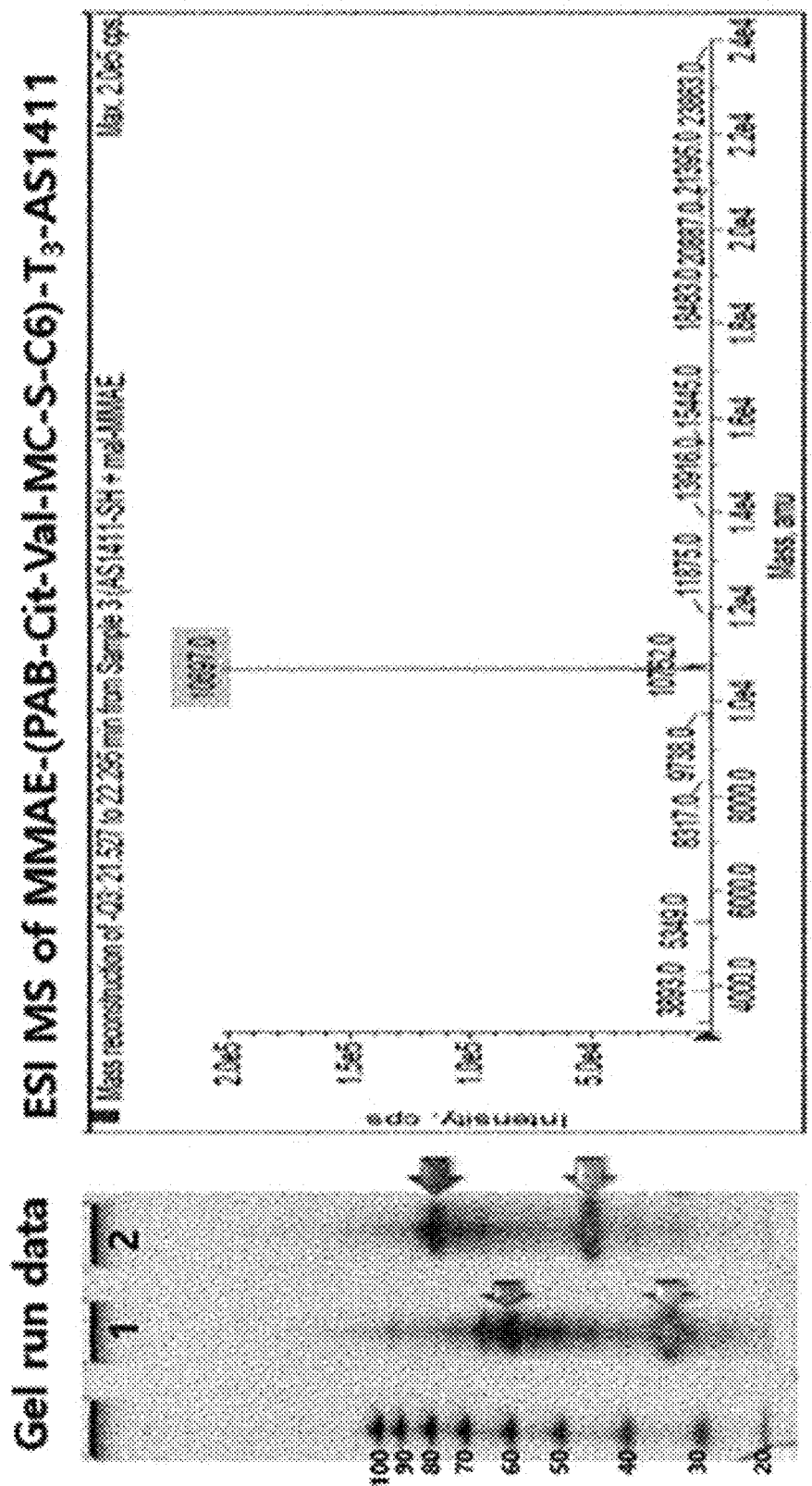
FIG. 1 illustrates Gel run data of HS-C6-$T_3$-AS1411 and MMAE-(PAB-Cit-Val-MC-S-C6)-$T_3$-AS1411 and ESI-MS of MMAE-(PAB-Cit-Val-MC-S-C6)-$T_3$-AS1411.

Synthesis of MMAE-(PAB-Cit-Val-MC-S-C6)-T$_3$-AS1411 from HS-C6-T$_3$-AS1411 was identified by Gel run, and a molecular weight of MMAE-(PAB-Cit-Val-MC-S-C6)-T$_3$-AS1411 was determined through ESI-MS (FIG. 1). $C_{364}H_{479}N_{120}O_{202}P_{29}S$ [Cal. MW=10697.69, Obs. MW=10697.0]

Example 2

Synthesis of MMAE-(PAB-Cit-Val-MC-S-C6)-T$_3$-CRO

By reacting maleimidocaproyl-valine-citrulline-p-aminobenzoyloxycarbonylmonomethyl auristatin E [MC-Val-Cit-PAB-MMAE] with HS-C6-tttcctcctcctccttctcctcctcctcc (SEQ ID NO: 3) [HS-C6-T$_3$-CRO], monomethyl auristatin E-p-aminobenzoyloxycarbonyl-citrulline-valine-Mal-S-C6-tttcctcctcctccttctcctcctcctcc (SEQ ID NO: 3) [MMAE-(PAB-Cit-Val-MC-S-C6)-T$_3$-CRO] was synthesized. In other words, RSS-C6-tttcctcctcctccttctcctcctcctcc (SEQ ID NO: 3) [RSS-C6-T$_3$-CRO) was subjected to reductive reaction in the presence of DTT for about 3 hours, and the remaining DTT was removed by a centrifuge and replaced with an SB17 buffer solution, resulting in HS-C6-tttcctcctcctccttctcctcctcctcc (SEQ ID NO: 3) [HS-C6-T$_3$-CRO). After putting MC-Val-Cit-PAB-MMAE dissolved in a small amount of DMSO into the resultant product, the mixture was shaken overnight. Separation/purification were performed through reverse phase HPLC (Waters-Xbridge OST C18 10×50 mm, 65, TEAE/CAN buffer).

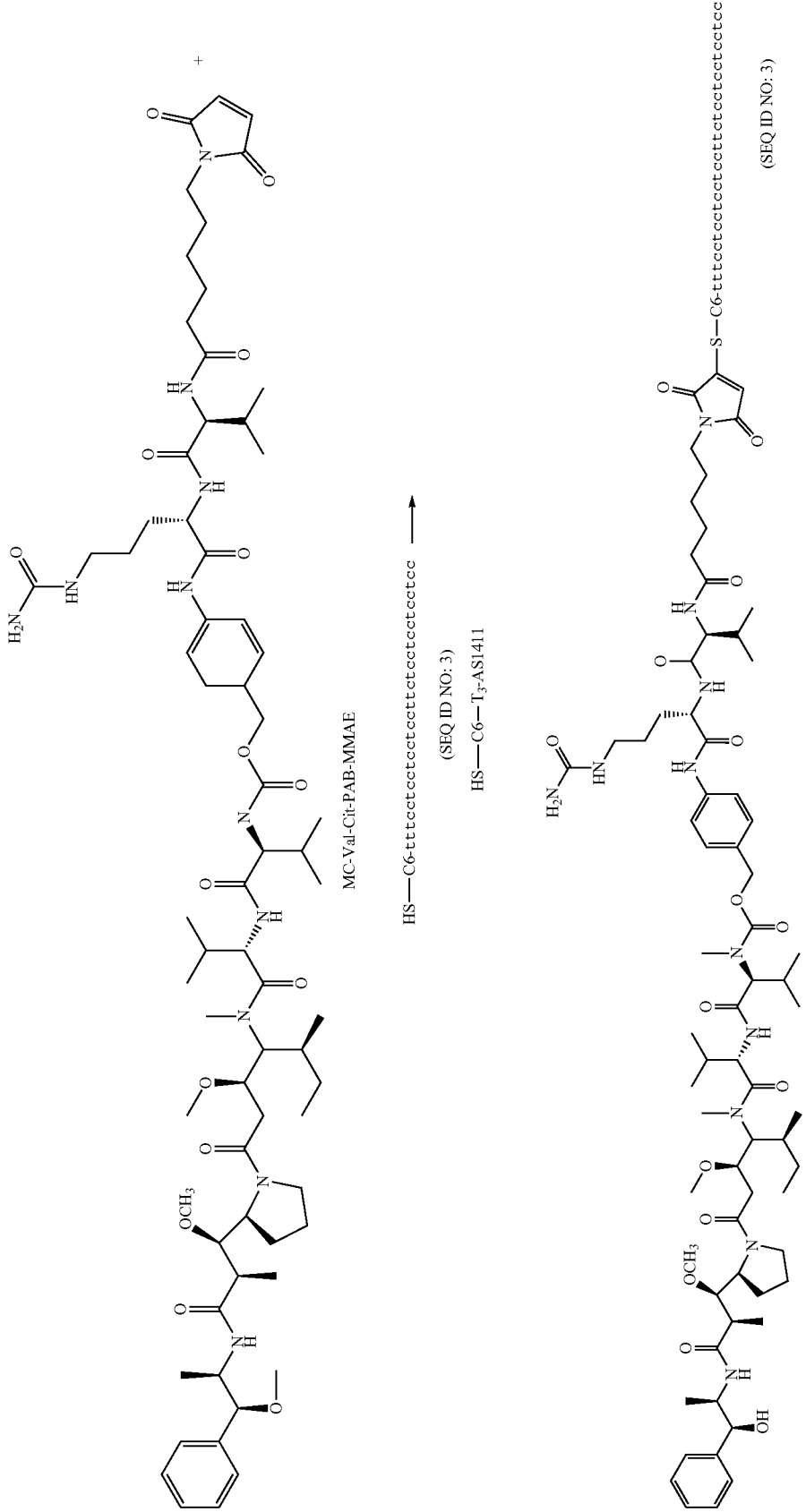

Figure 2:
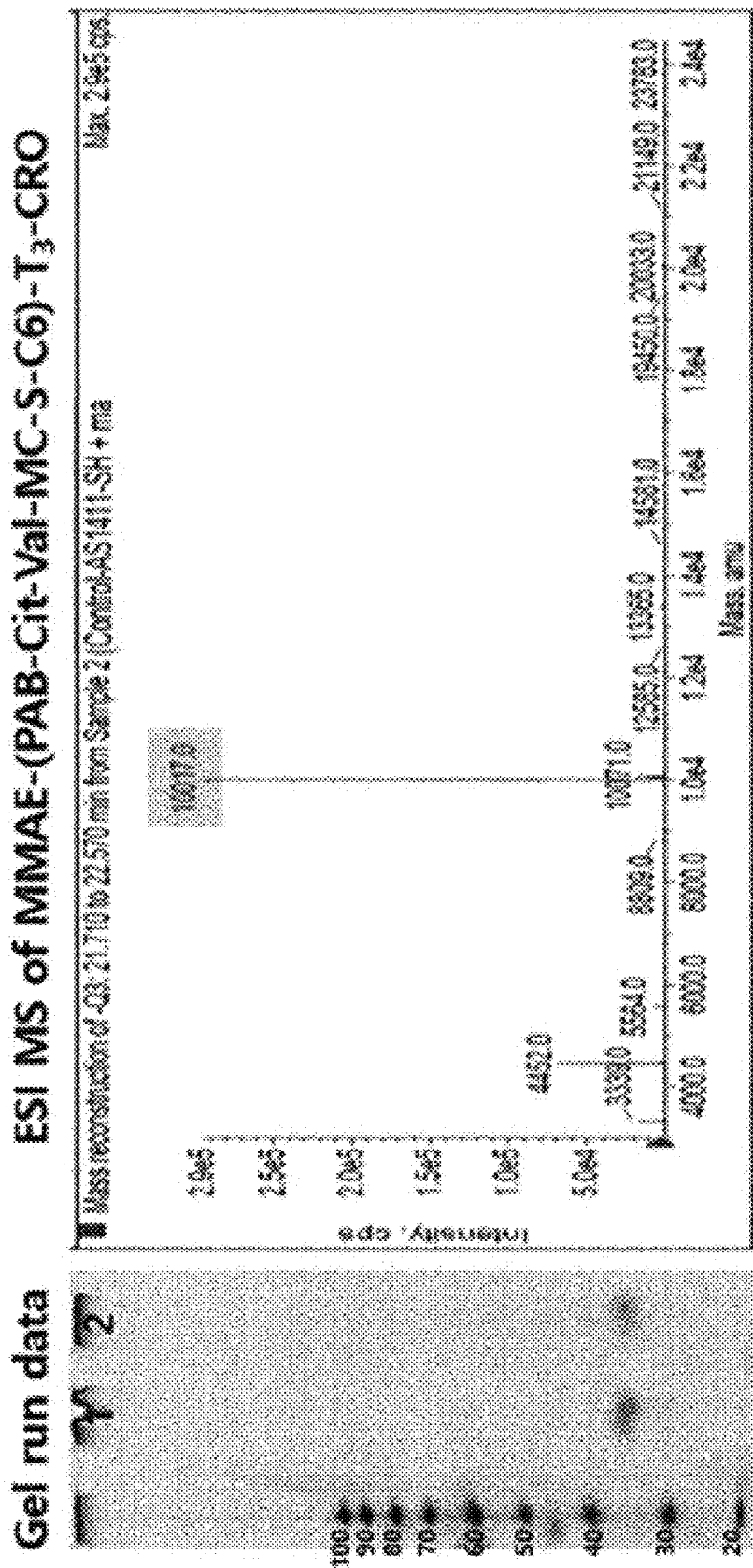
FIG. 2 illustrates Gel run data of HS-C6-$T_3$-CRO and MMAE-(PAB-Cit-Val-MC-S-C6)-$T_3$-CRO and ESI-MS of MMAE-(PAB-Cit-Val-MC-S-C6)-$T_3$-CRO.

MMAE-(PAB-Cit-Val-MC-S-C6)-T$_3$-CRO was synthesized by reaction of MC-Val-Cit-PAB-MMAE and HS-C6-T$_3$-CRO Synthesis of MMAE-(PAB-Cit-Val-MC-S-C6)-T$_3$-CRO from HS-C6-T$_3$-CRO was identified by Gel run, and a molecular weight of MMAE-(PAB-Cit-Val-MC-S-C6)-T$_3$-CRO was determined through ESI-MS (FIG. 2). C$_{347}$H$_{479}$N$_{86}$O$_{202}$P$_{29}$S [Cal. MW=10018.13, Obs. MW=10017.28]

Example 3

Synthesis of 12,13-(MMAE-PAB-Cit-Val-MC-S-C6)$_2$-AS1411 and 12 or 13-(MMAE-PAB-Cit-Val-MC-S-C6)-AS1411

By reacting maleimidocaproyl-valine-citrulline-p-aminobenzoyloxycarbonylmonomethyl auristatin E [MC-Val-Cit-PAB-MMAE] with ggtggtggtggu (SEQ ID NO: 4)[5-N-(6-(3-thiopropanoyl)-aminohexyl)-3-acrylamido]u[5-N-(6-(3-thiopropanoyl)-aminohexyl)-3-acrylamido]gtggtggtggtgg (SEQ ID NO: 6)[12,13-(HS-C6)$_2$-AS1411], ggtggtggtggu (SEQ ID NO: 4)[5-N-(6-(3-monomethyl auristatin-p-aminobenzoyloxycarbonyl-citrulline-valine-Mal-thiopropanoyl)-aminohexyl)-3-acrylamido]u[5-N-(6-(3-monomethyl auristatin-p-aminobenzoyloxycarbonyl-citrulline-valine-Mal-thiopropanoyl)-aminohexyl)-3-acrylamido]gtggtggtggtgg (SEQ ID NO: 6)[12,13-(MMAE-PAB-Cit-Val-MC-S-C6)$_2$-AS1411], and ggtggtggtggu (SEQ ID NO: 4)[5-N-(6-(3-monomethyl auristatin-p-aminobenzoyloxycarbonyl-citrulline-valine-Mal-thiopropanoyl)-aminohexyl)-3-acrylamido]ugtggtggtggtgg (SEQ ID NO: 5)][12 or 13-(MMAE-PAB-Cit-Val-MC-S-C6)-AS1411] were synthesized. In other words, ggtggtggtggu (SEQ ID NO: 4)[5-N-(6-(3-benzoyl thiopropanoyl)-aminohexyl)-3-acrylamido]u[5-N-(6-(3-benzoyl thiopropanoyl)-aminohexyl)-3-acrylamido]gtggtggtggtgg (SEQ ID NO: 6)[12,13-(Bz-S-C6)$_2$-AS1411] was subjected to reductive reaction in the presence of DTT for about 3 hours, and the remaining DTT was removed by a centrifuge and replaced with an SB17 buffer solution, resulting in ggtggtggtggu (SEQ ID NO: 4) [5-N-(6-(3-thiopropanoyl)-aminohexyl)-3-acrylamido]u[5-N-(6-(3-thiopropanoyl)-aminohexyl)-3-acrylamido]gtggtggtggtgg (SEQ ID NO: 6) [12,13-(HS-C6)$_2$-AS1411]. After putting MC-Val-Cit-PAB-MMAE dissolved in a small amount of DMSO into the resultant product, the mixture was shaken overnight. Separation/purification were performed through reverse phase HPLC (Waters-Xbridge OST C18 10×50 mm, 65, TEAE/CAN buffer), thereby yielding 12,13-(MMAE-PAB-Cit-Val-MC-S-C6)$_2$-AS1411 and 12 or 13-(MMAE-PAB-Cit-Val-MC-S-C6)-AS1411.

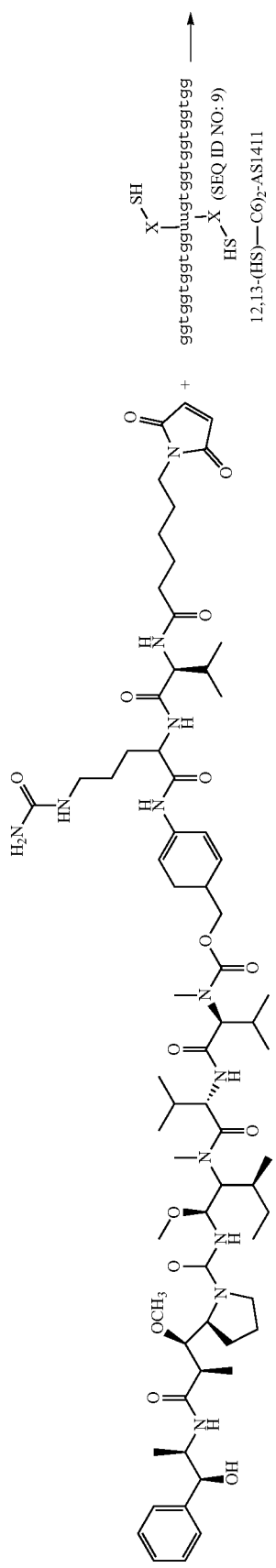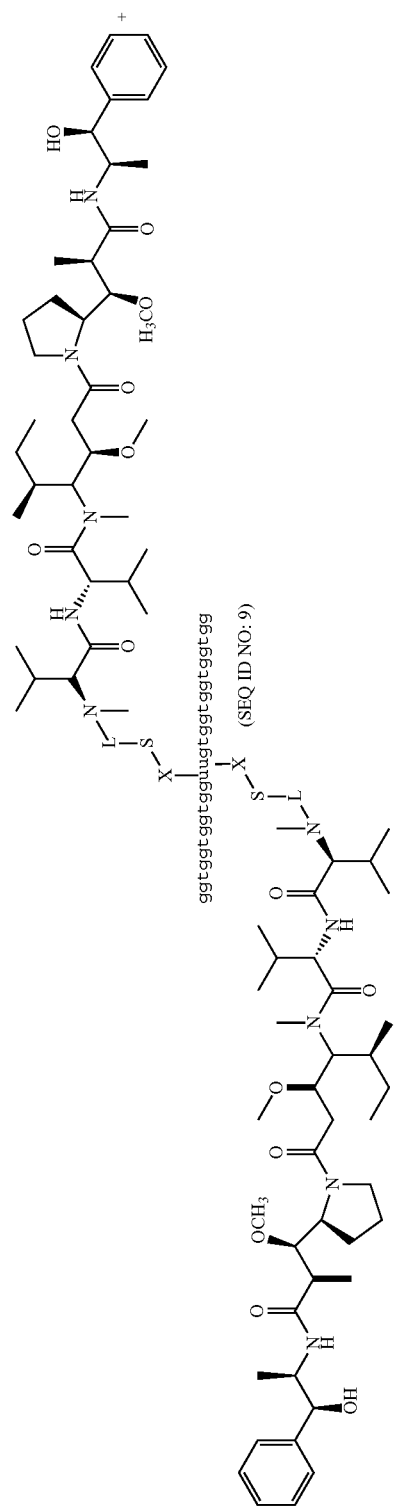

-continued
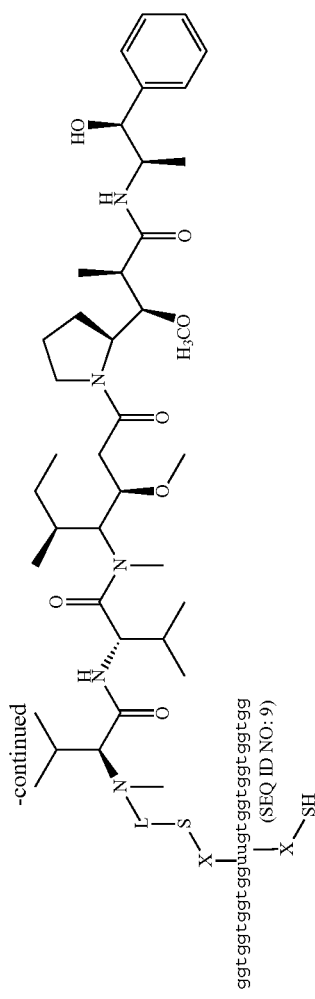
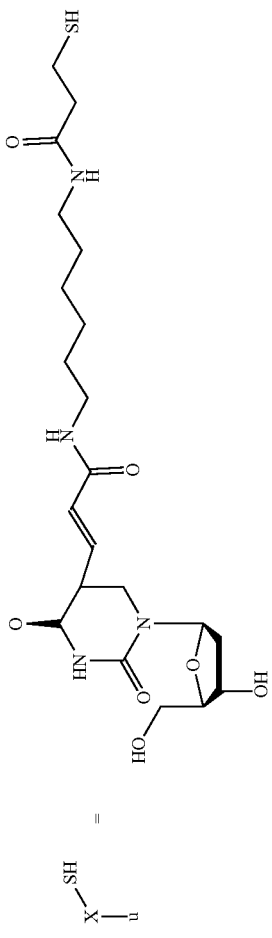
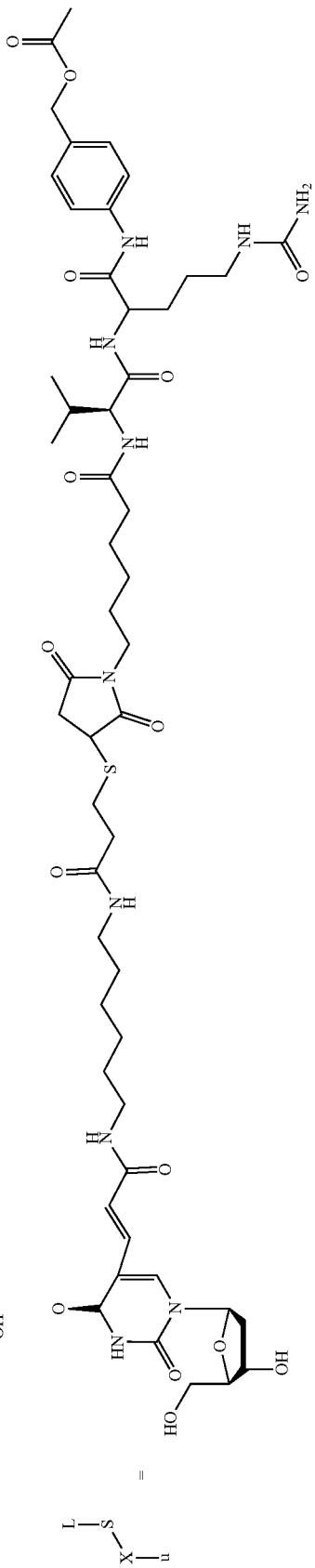
ggtggtggtggtuugtgggtggtgg
(SEQ ID NO: 9)
12 or 13-(MMAE-PAB-Cit-Val-MC-S-C6)3-AS1411 Conjugate 12,13-(MMAE-PAB-Cit-Val-MC-S-C6)$_2$-AS1411 and 12 or 13-(MMAE-PAB-Cit-Val-MC-S-C6) were synthesized by reaction of MC-Val-Cit-PAB-MMAE and 12,13-(HS-C6)$_2$-AS1411

Figure 3:
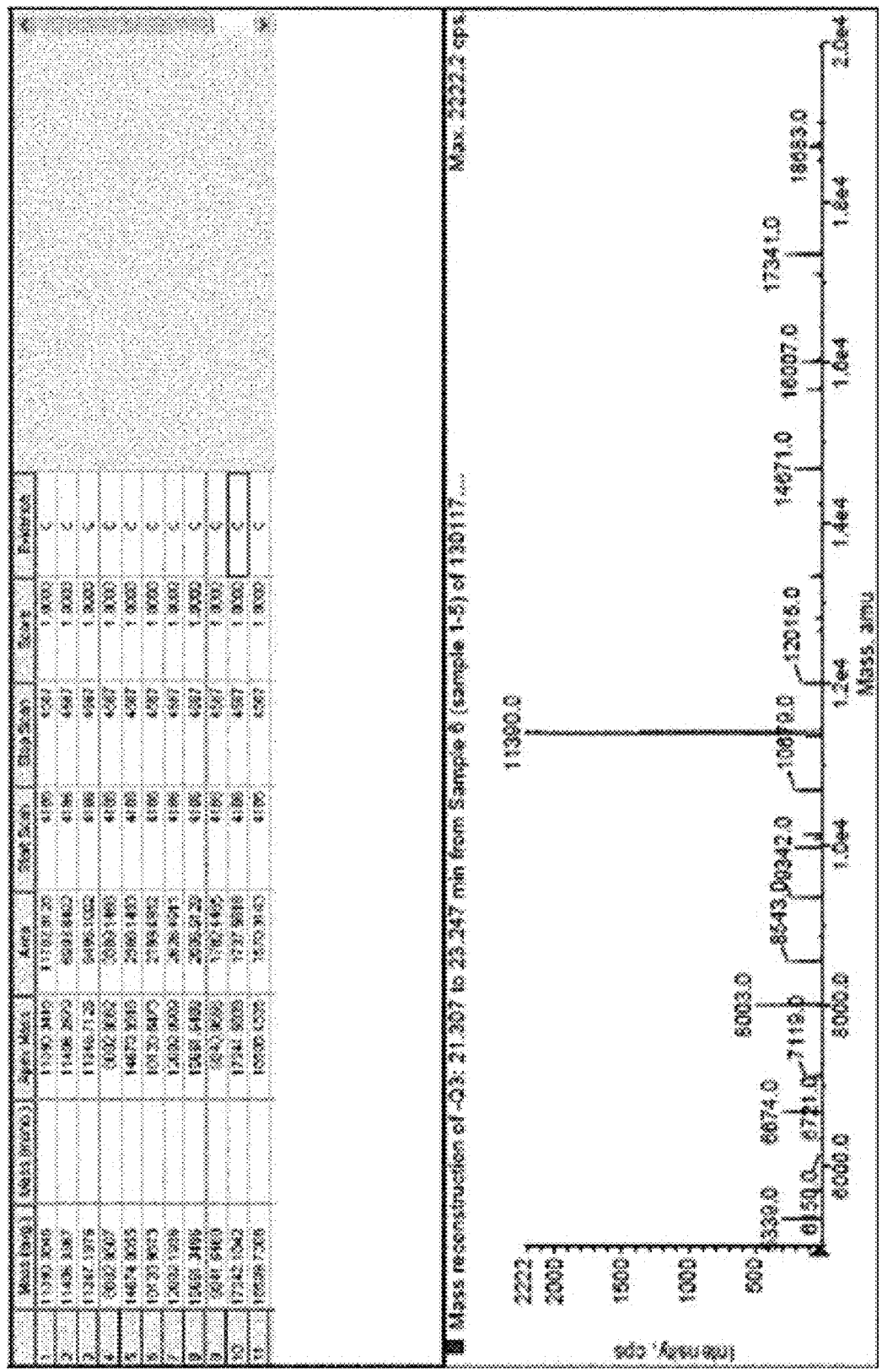
FIG. 3 illustrates MSI-MS of 12,13-(MMAE-PAB-Cit-Val-MC-S-C6)$_2$-AS1411.
Figure 4:
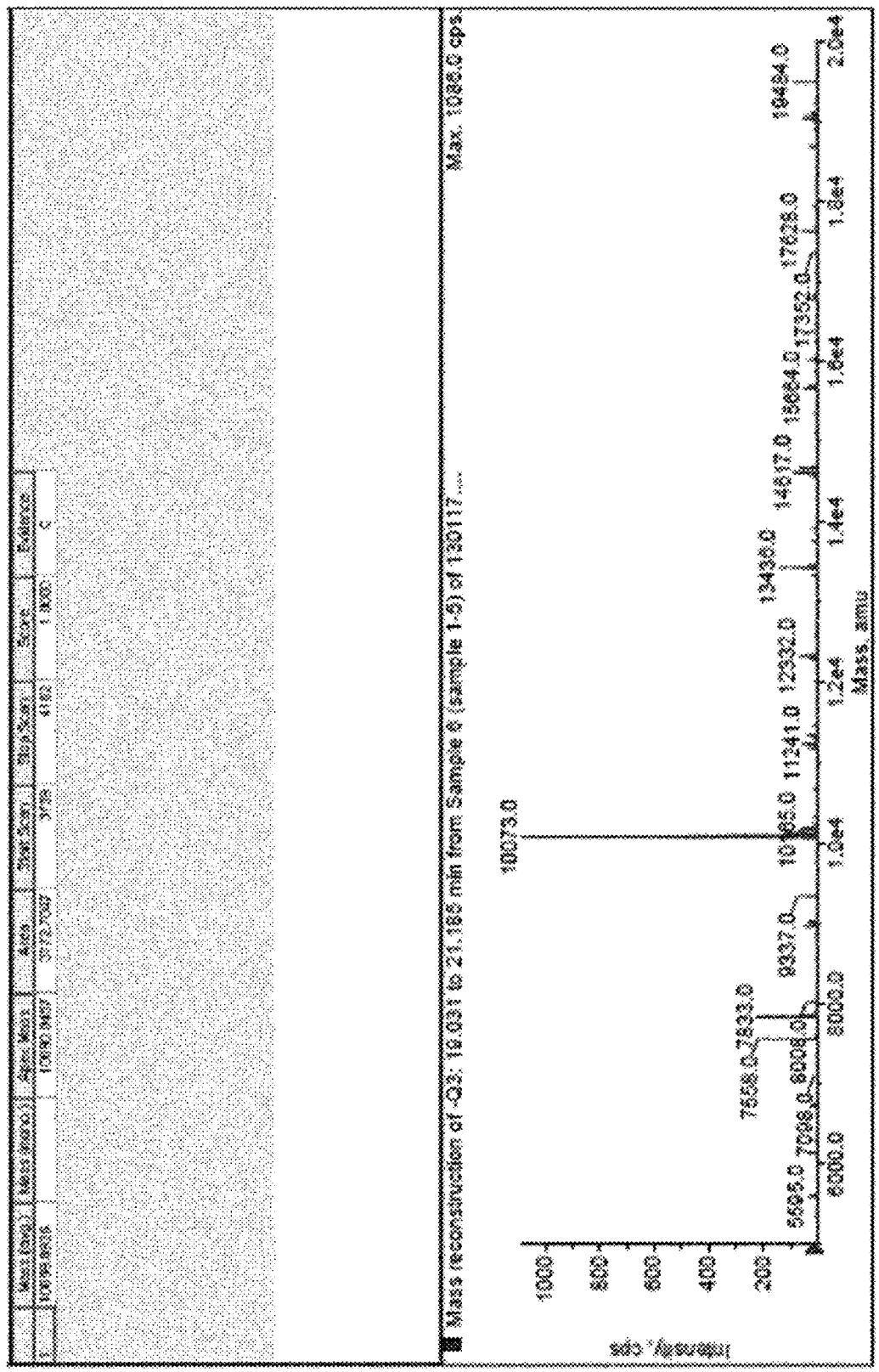
FIG. 4 illustrates ESI-MS of 12 or 13-(MMAE-PAB-Cit-Val-MC-S-C6)-AS1411.

Through ESI-MS, molecular weights of 12,13-(MMAE-PAB-Cit-Val-MC-S-C6)$_2$-AS1411 and 12 or 13-(MMAE-PAB-Cit-Val-MC-S-C6)-AS1411 were determined (FIG. 3 and FIG. 4). 12,13-(MMAE-PAB-Cit-Val-MC-S-C6)$_2$-AS1411, C$_{418}$H$_{568}$N$_{129}$O$_{197}$P$_{25}$S$_2$ [Cal. MW=11390.21, Obs. MW=11390.0]; 12 or 13-(MMAE-PAB-Cit-Val-MC-S-C6)-AS1411, C$_{350}$H$_{463}$N$_{118}$O$_{182}$P$_{25}$S$_2$ [Cal. MW=10073.58, Obs. MW=10073.0]

Example 4

Synthesis of Citravin-(GLFG-MC-S-C6)-T$_3$-AS1411 Conjugate

By reacting maleimidocaproyl-(Gly-Phe-Leu-Gly (SEQ ID NO: 7))-citravin [MC-GFLG-citravin] with HS-C6-tttggtggtggtggttgtggtggtggtgg (SEQ ID NO: 2) [HS-C6-T$_3$-AS1411], citravin-(Gly-Leu-Phe-Gly (SEQ ID NO: 8))-Mal-S-C6-tttggtggtggtggttgtggtggtggtgg (SEQ ID NO: 2) [Citravin-(GLFG-MC-S-C6)-T$_3$-AS1411] was synthesized. In other words, RSS-C6-tttggtggtggtggttgtggtggtggtgg (SEQ ID NO: 2) [RSS-C6-T$_3$-AS141] was subjected to reductive reaction in the presence of DTT for about 3 hours, and the remaining DTT was removed by a centrifuge and replaced with an SB17 buffer solution. After putting Mal-GPLG-citravin dissolved in a small amount of DMSO into the resultant product, the mixture was shaken overnight. Separation/purification were performed through reverse phase HPLC (Waters-Xbridge OST C18 10×50 mm, 65, TEAE/CAN buffer), thereby yielding citravin-(GLFG-MC-S-C6)-T$_3$-AS1411. Through ESI-MS, a molecular weight of citravin-(GLFG-MC-S-C6)-T$_3$-AS1411 was determined. C$_{334}$H$_{424}$N$_{117}$O$_{199}$P$_{29}$S [Cal. MW=10191.91, Obs. MW=10190.88]

MC-GFLG-Cytarabine

HS—C6-tttggtggtggtggttgtggtggtggtgg ⟶

(SEQ ID NO: 2)

HS—C6—T$_3$-AS1411

Cytarabine-(GLFG-MC-S-C6)-T$_3$-AS1411 Conjugate (SEQ ID NO: 2)

Citravin-(GLFG-MC-S-C6)-T$_3$-AS1411 was synthesized by reaction of C-GFLG-citravin and HS-C6-T$_3$-AS1411

Example 5

Synthesis of 12,13-(citravin-GLFG-MC-S-C6)$_2$-AS1411 Conjugate and 12 or 13-(citravin-GLFG-MC-S-C6)-AS1411 Conjugate By reacting maleimidocapryl-(Gly-Phe-Leu-Gly (SEQ ID NO: 7))-citravin [MC-GFLG-citravin] with ggtggtggtggu (SEQ ID NO: 4) [5-N-(6-(3-thiopropanoyl)-aminohexyl)-3-acrylamido]u[5-N-(6-(3-thiopropanoyl)-aminohexyl)-3-acrylamido]gtggtggtggtgg (SEQ ID NO: 6) [12,13-(HS-C6)$_2$-AS1411], ggtggtggtggu (SEQ ID NO: 4) [citravin-Gly-Leu-Phe-Gly (SEQ ID NO: 8)-Mal-thiopropanoyl)-aminohexyl)-3-acrylamido]u[citravin-Gly-Leu-Phe-Gly (SEQ ID NO: 8)-Mal-thiopropanoyl)-aminohexyl)-

3-acrylamido]gtggtggtggtgg (SEQ ID NO: 6) [12,13-(citravin-GLFG-MC-S-C6)$_2$-AS1411] and ggtggtggtggu (SEQ ID NO: 4) [citravin-Gly-Leu-Phe-Gly (SEQ ID NO: 8)-Mal-thiopropanoyl)-aminohexyl)-3-acrylamido] ugtggtggtggtgg (SEQ ID NO: 5)][12 or 13-(citravin-GLFG-MC-S-C6)-AS1411] were synthesized. In other words, ggtggtggtggu (SEQ ID NO: 4) [5-N-(6-(3-benzoyl thiopropanoyl)-aminohexyl)-3-acrylamido]u[5-N-(6-(3-benzoyl thiopropanoyl)-aminohexyl)-3-acrylamido]gtggtggtggtgg (SEQ ID NO: 6) [12,13-(Bz-S-C6)$_2$-AS1411] was subjected to reductive reaction in the presence of DTT for about 3 hours, and the remaining DDT was removed by a centrifuge and replaced with an SB17 buffer solution, resulting in ggtggtggtggu (SEQ ID NO: 4) [5-N-(6-(3-thiopropanoyl)-aminohexyl)-3-acrylamido]u[5-N-(6-(3-thiopropanoyl)-aminohexyl)-3-acrylamido]gtggtggtggtgg (SEQ ID NO: 6) [12,13-(HS-C6)$_2$-AS1411]. After putting MC-GFLG-citravin dissolved in a small amount of DMSO into the resultant product, the mixture was shaken overnight. Purification was performed through reverse phase HPLC (Waters-Xbridge OST C18 10 X 50 mm, 65, TEAE/CAN buffer), thereby yielding 12,13-(citravin-GLFG-MC-S-C6)$_2$-AS1411 and 12 or 13 (citravin-GLFG-MC-S-C6)-AS1411. Through ESI-MS, molecular weights of each of the above products were determined: 12,13-(citravin-GLFG-MC-S-C6)$_2$-AS1411, $C_{358}H_{458}N_{123}O_{191}P_{25}S_2$ [Cal. MW=10378, 66 Obs. MW=10379.23]; 12 or 13 (citravin-GLFG-MC-S-C6)-AS1411, $C_{320}H_{408}N_{115}O_{179}P_{25}S_2$ [Cal. MW=9567.81, Obs. MW=9568.09]

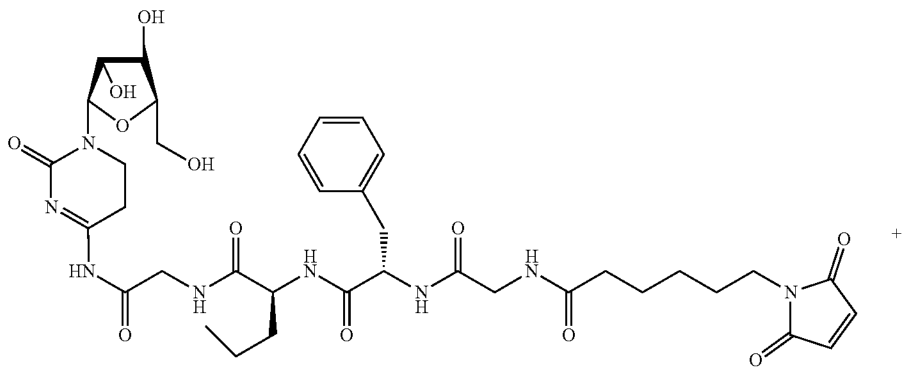

MC-GFLG-Cytarabine 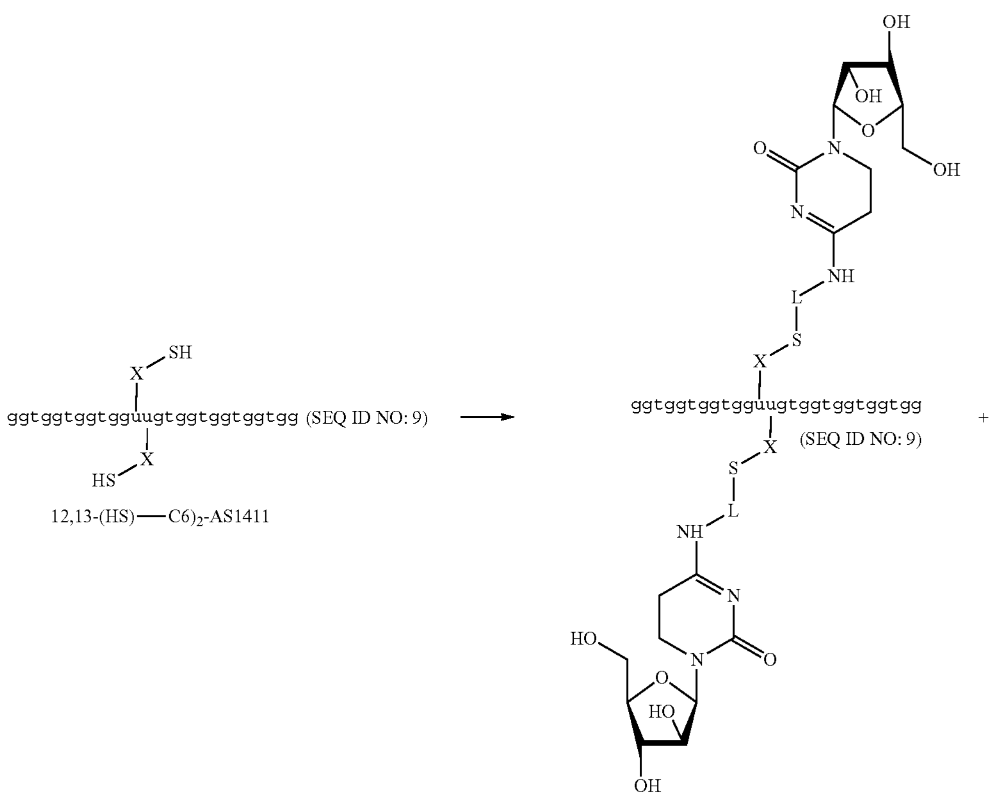 12,13-(Cytarabine-GLFG-MC-S-C6)$_3$-AS1411 Conjugate 12,13-(citravin-GLFG-MC-S-C6)$_2$-AS1411 and 12 or 13 (citravin-GLFG-MC-S-C6)-AS1411 were synthesized by reaction of MC-GFLG-citravin and 12,13-(HS-C6)$_2$-AS1411

Example 6

In Vitro Efficacy Validation

Figure 5:
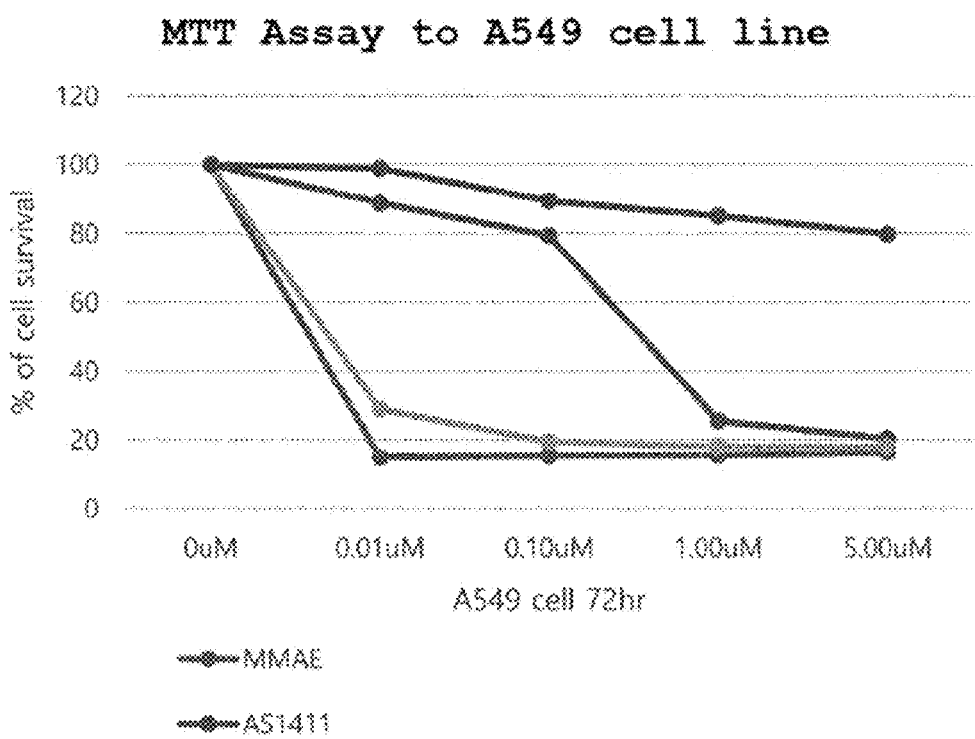
FIG. 5 illustrates MTT assay results of MMAE-(PAB-Cit-Val-MC-S-C6)-$T_3$-AS1411 and MMAE-(PAB-Cit-Val-MC-S-C6)-$T_3$-CRO to A549 cell lines.

MTT Assay of MMAE-(PAB-Cit-Val-MC-S-C6)-T$_3$-AS1411 and MMAE-(PAB-Cit-Val-MC-S-C6)-T$_3$-CRO to A549 Cell Lines With regard to A549 cell line as a lung cancer cell line over-expressing a nucleoline protein, cell inhibition efficacy of MMAE-(PAB-Cit-Val-MC-S-C6)-T$_3$-AS1411 was verified in vitro by MTT assay. When comparing cell viability and cell proliferation of the cells through MTT assay of MMAE, AS1411, MMAE-(PAB-Cit-Val-MC-S-C6)-T$_3$-AS1411 and MMAE-(PAB-Cit-Val-MC-S-C6)-T$_3$-CRO, respectively, it was demonstrated that MMAE-(PAB-Cit-Val-MC-S-C6)-T$_3$-AS1411 has almost the same efficacy as MMAE. A549 cells (ATCC, IMDM+10% FBS) were seeded on a 96-well plate in a cell number of 2.5 to 5×10$^5$ cells/well, which was determined by a cell test method to determine an appropriate cell concentration, followed by growing for 1 day. After heating each of MMAE-(PAB-Cit-Val-MC-S-C6)-T$_3$-AS1411 and MMAE-(PAB-Cit-Val-MC-S-C6)-T$_3$-CRO at 95° C. for 5 minutes, the heated product was gradually cooled at room temperature and directly treated on each well at different concentrations. After incubating the treated A549 cells in 5% CO$_2$ incubator for 72 hours, the incubated product was treated with 20 μL of a reagent solution for MTT assay (Cell Proliferation kit II, Roche) and incubated for different periods of time (10 min, 30 min, 1 hr). Thereafter, the final product was subjected to measurement of absorbance at 490 nm by an ELISA reader (FIG. 5).

Example 7

Figure 6:
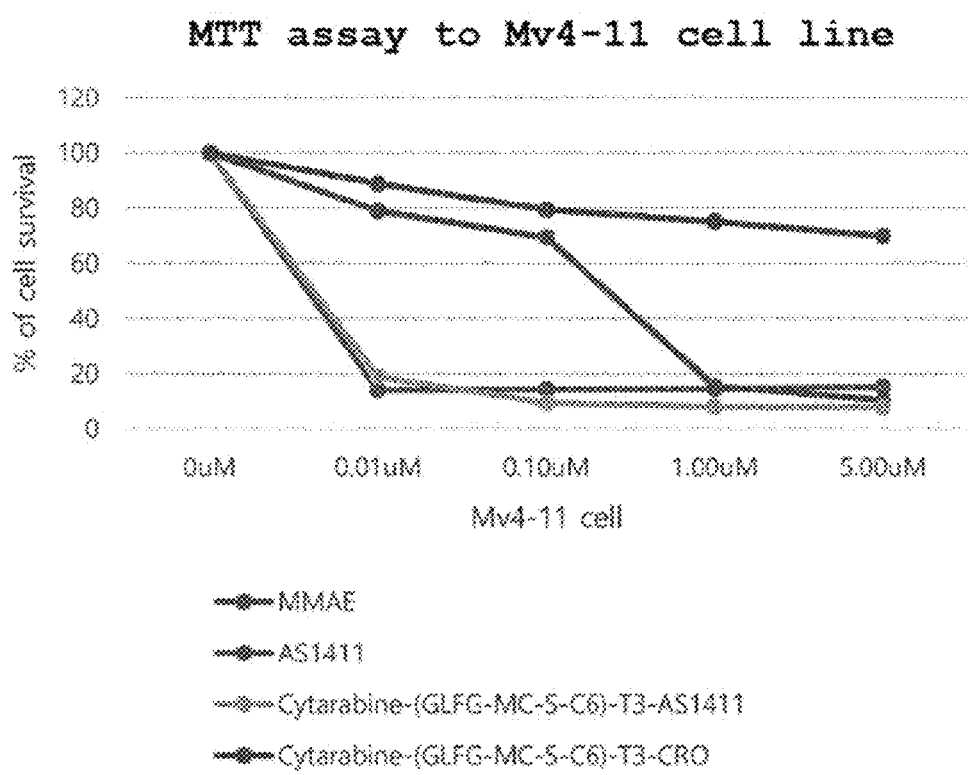
FIG. 6 illustrates MTT assay results of citravin-(GLFG-MC-S-C6)-$T_3$-AS1411 and citravin-(GLFG-MC-S-C6)-$T_3$-CRO to Mv4-11 cell lines.

MTT Assay of Citravin-(GLFG-MC-S-C6)-T$_3$-AS1411 and Citravin-(GLFG-MC-S-C6)-T$_3$-CRO to Mv4-11 Cell Lines With regard to Mv4-11 cell line as a lung cancer cell line over-expressing a nucleoline protein, cell inhibition efficacy of citravin-(GLFG-MC-S-C6)-T$_3$-AS1411 was verified in vitro by MTT assay. When comparing cell viability and cell proliferation of the cells through MTT assay of citravin, AS1411, citravin-(GLFG-MC-S-C6)-$T_3$-AS1411 and citravin-(GLFG-MC-S-C6)-$T_3$-CRO, respectively, it was demonstrated that citravin-(GLFG-MC-S-C6)-$T_3$-AS1411 conjugate has almost the same efficacy as citravin. Mv4-11 cells (ATCC, IMDM+10% FBS) were seeded on a 96-well plate in a cell number of 2.5 to 5×10$^5$ cells/well, which was determined by a cell test method to determine an appropriate cell concentration, followed by growing for 1 day. After heating each of citravin-(GLFG-MC-S-C6)-$T_3$-AS1411 and citravin-(GLFG-MC-S-C6)-$T_3$-CRO at 95° C. for 5 minutes, the heated product was gradually cooled at room temperature and directly treated on each well at different concentrations. After incubating the treated A549 cells in 5% $CO_2$ incubator for 72 hours, the incubated product was treated with 20 µL of a reagent solution for MTT assay (Cell Proliferation kit II, Roche) and incubated for different periods of time (10 min, 30 min, 1 hr). Thereafter, the final product was subjected to measurement of absorbance at 490 nm by an ELISA reader (FIG. 6).

Example 8

In Vivo Efficacy Validation

Figure 7:
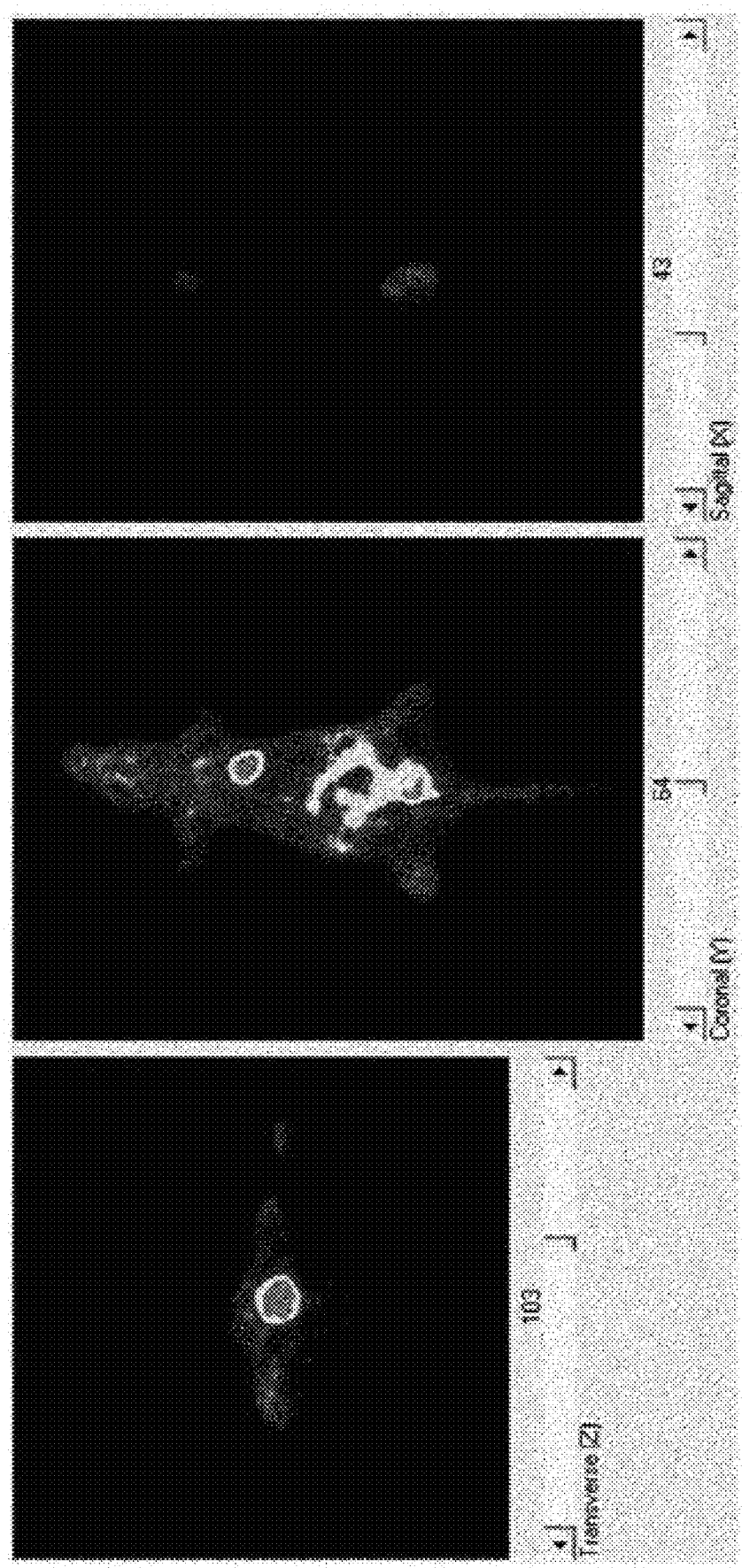
FIG. 7 illustrates FDG PET images obtained before treatment of A549 lung cancer cell line-injected mice (a tumor with FDG intake in the left thigh region is observed).
Figure 8:
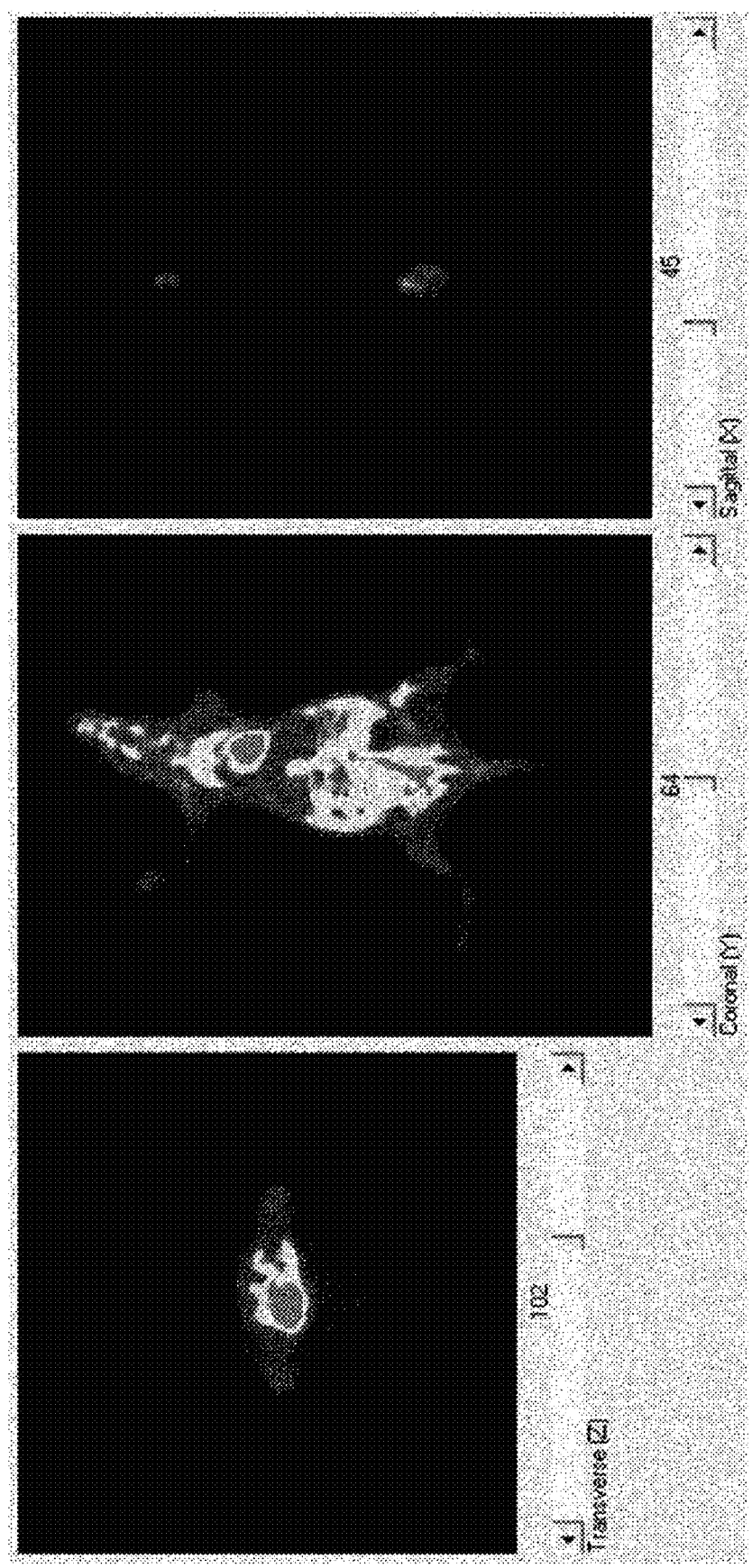
FIG. 8 illustrates FDG PET images obtained 30 days after treatment of A549 lung cancer cell line-injected mice with MMAE-(PAB-Cit-Val-MC-S-C6)-$T_3$-AS1411 (a decrease in FDG intake in the tumor is observed).

Validation of In Vivo Therapeutic Efficacy of MMAE-(PAB-Cit-Val-MC-S-C6)-$T_3$-AS1411 on A549 Lung Cancer Cell Line-Injected Mice To A549 lung cancer cell line-injected mice, MMAE-(PAB-Cit-Val-MC-S-C6)-$T_3$-AS1411 and MMAE, respectively, were administered by IV injection for 30 days, followed by identifying tumor sizes through PET images. A549 lung cancer cells in a number of 6.1×10$^6$ cells/ml were injected subcutaneously in the right thigh of each nude mouse. The tumor size was measured in 3 to 4 weeks after the injection and, when a diameter of the tumor reached 0.8 cm, microPET images were captured before treatment. For PET images, F-18 FDG 0.2 mCi was i.p. injected and then the images were captured (Siemens Inveon). After detection of FDG intake in the tumor from the images, MMAE-(PAB-Cit-Val-MC-S-C6)-$T_3$-AS1411 was i.v. injected in an experimental group of 5 mice 4 times by 5 day intervals (7.5 mg/kg, 0.5 mg/kg of MMAE). After 30 days from the start of treatment, microPET images were captured by the same method as used before treatment. After administration of MMAE-(PAB-Cit-Val-MC-S-C6)-$T_3$-AS1411 to A549 lung cancer cell line-injected mice for 30 days through IV injection, it was identified from PET images that FDG intake in the tumor remarkably decreased (FIG. 7 and FIG. 8).

Example 9

Figure 9:
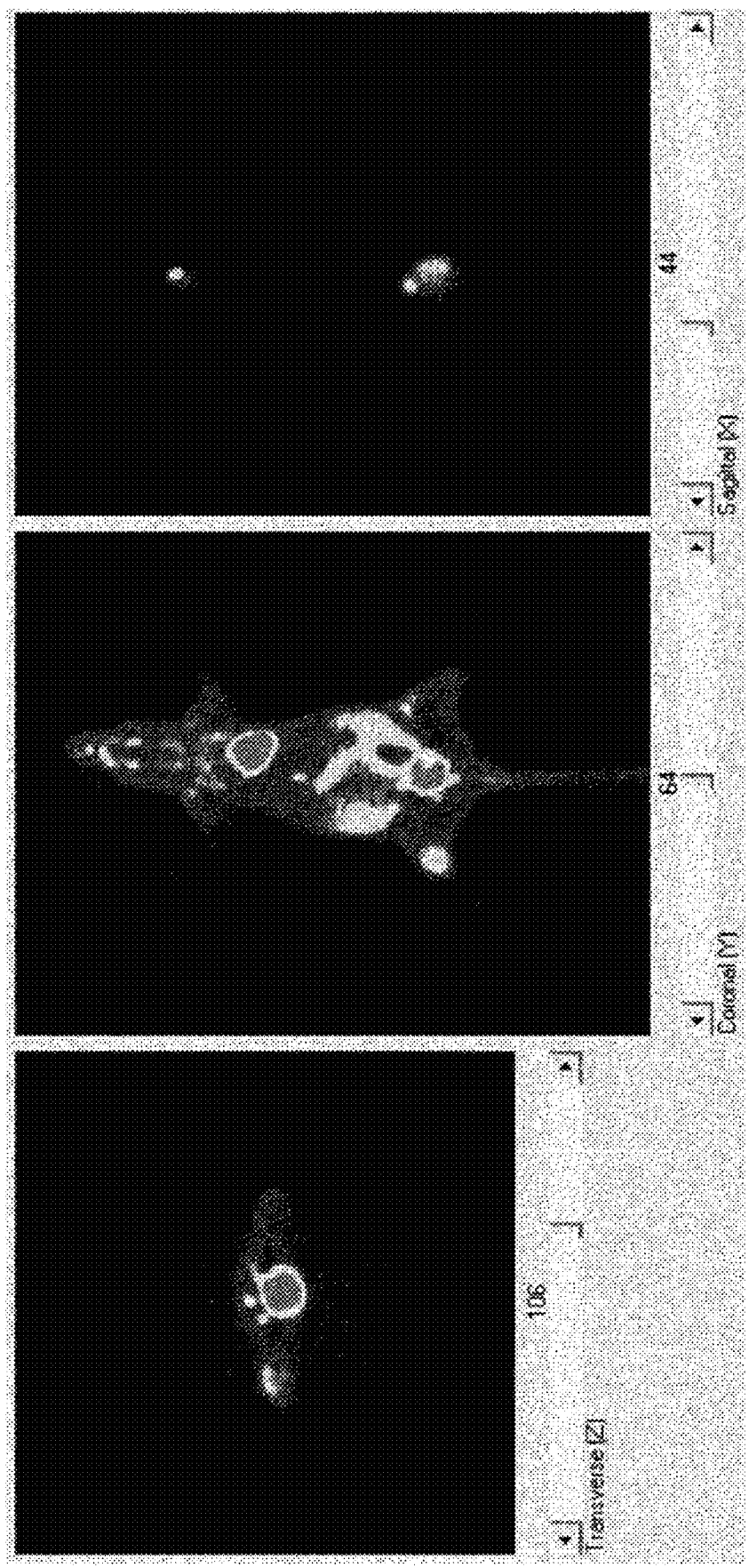
FIG. 9 illustrates FDG PET images obtained before treatment of A549 lung cancer cell line-injected mice (a tumor with FDG intake in the left thigh region is observed).
Figure 10:
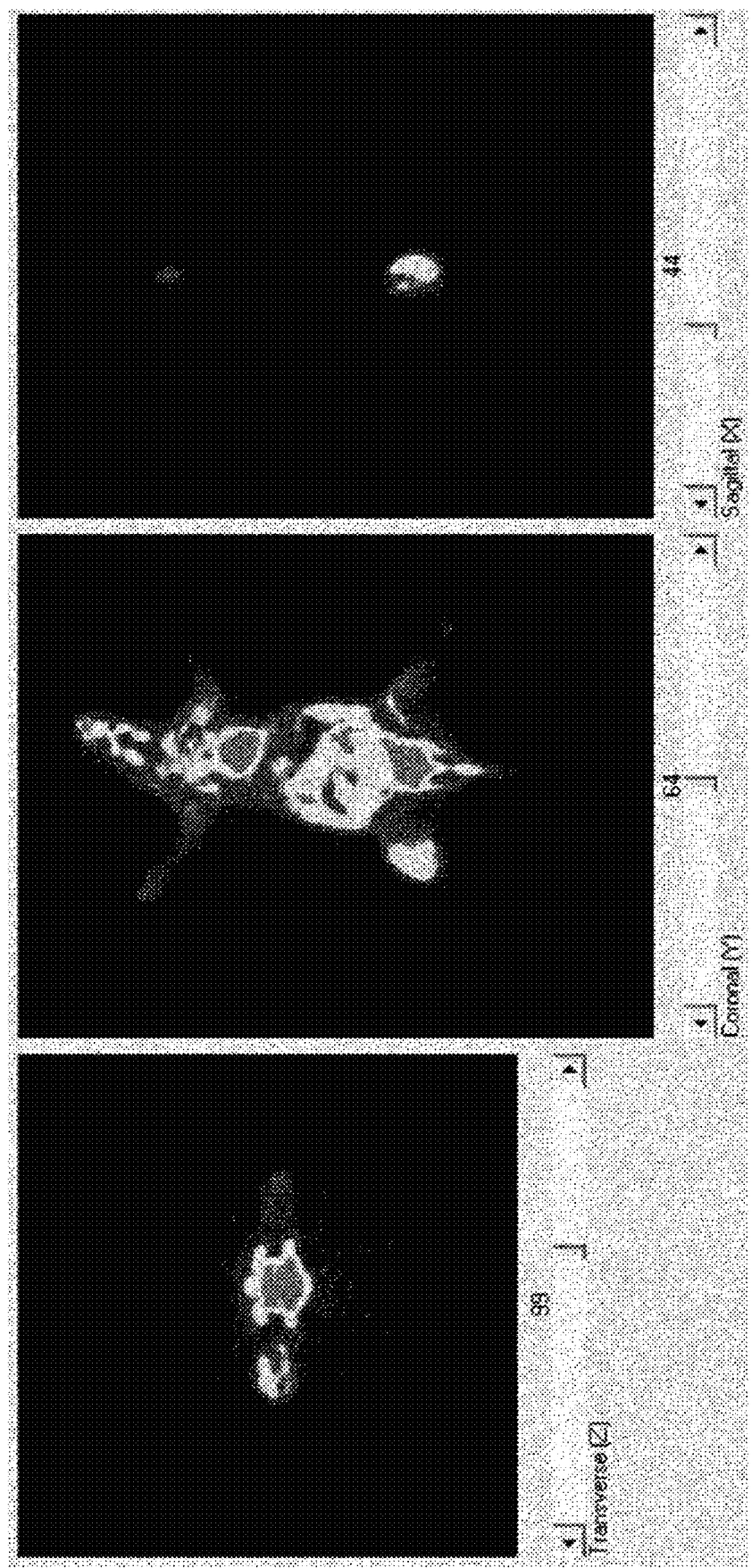
FIG. 10 illustrates FDG PET images obtained 30 days after treatment of A549 lung cancer cell line-injected mice with MMAE (an increase in FDG intake in the tumor is observed).

Validation of In Vivo Therapeutic Efficacy of MMAE on A549 Lung Cancer Cell Line-Injected Mice To A549 lung cancer cell-injected mice, MMAE was administered by IV injection for 30 days, followed by observation of PET images. A549 lung cancer cells in a number of 6.1×10$^6$ cells/ml were injected subcutaneously in the right thigh of each nude mouse. The tumor size was measured in 3 to 4 weeks after the injection and, when a diameter of the tumor reached 0.8 cm, microPET images were captured before treatment. For PET images, F-18 FDG 0.2 mCi was i.p. injected and then the images were captured (Siemens Inveon). After detection of FDG intake in the tumor from the images before treatment, MMAE was i.v. injected in an experimental group of 5 mice 4 times by 5 day intervals (0.5 mg/kg). After 30 days from the start of treatment, microPET images were captured by the same method as used before treatment. Compared to before MMAE treatment, it was identified from FDG PET images that FDG intake in the tumor was increased even after treatment (FIG. 9 and FIG. 10).

Example 10

Ex-Vivo Validation

Figure 11:
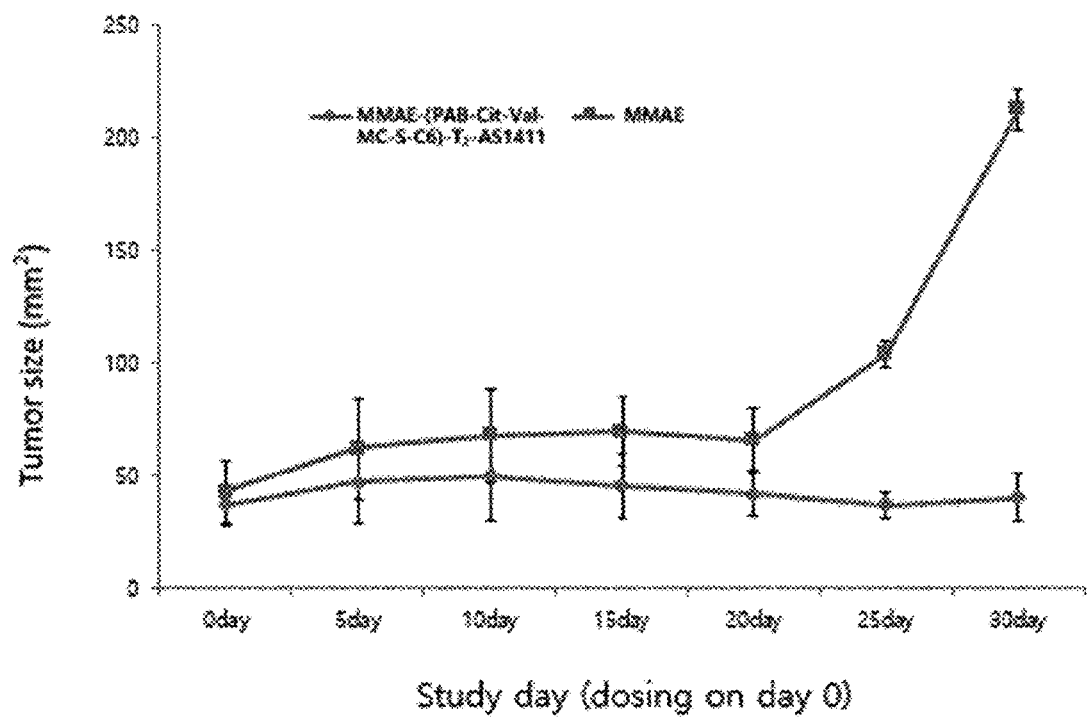
FIG. 11 illustrates comparison of tumor sizes measured after treatment using MMAE-(PAB-Cit-Val-MC-S-C6)-$T_3$-AS1411 and MMAE, respectively, in A549 tumor model.
Figure 12:
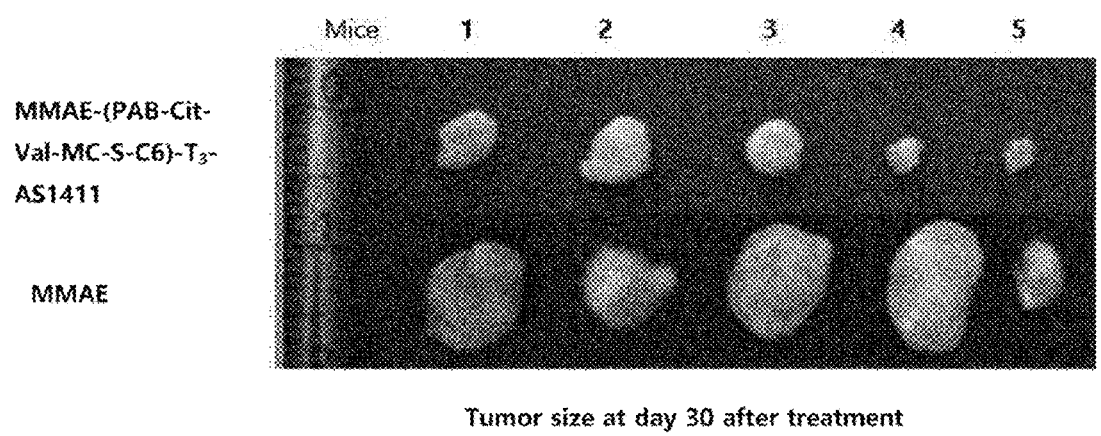
FIG. 12 illustrates comparison of sizes of tumors excised 30 days after treatment using MMAE-(PAB-Cit-Val-MC-S-06)-$T_3$-AS1411 and MMAE, respectively, in A549 tumor model.

As compared to administration of MMAE alone, administration of MMAE-(PAB-Cit-Val-MC-S-C6)-$T_3$-AS1411 to A549 lung cancer cell line-injected mice exhibited superior cancer inhibitory efficacy. As compared to administration of MMAE alone, it was determined that MMAE-(PAB-Cit-Val-MC-S-C6)-$T_3$-AS1411 inhibits 80% more cancer. After the start of treatment, sizes of tumors were measured in both of horizontal and vertical axes by 5 day intervals. 30 days after the treatment, tumors were excised from separate groups. As shown in the pictures below, each group was photographed and the tumor sizes were compared between MMAE-(PAB-Cit-Val-MC-S-C6)-$T_3$-AS1411 and MMAE (FIG. 11 and FIG. 12).

As a result of verifying in vivo efficacies of MMAE-(PAB-Cit-Val-MC-S-C6)-$T_3$-AS1411 and MMAE to A549 cell lines, it was demonstrated that MMAE-(PAB-Cit-Val-MC-S-C6)-$T_3$-AS1411 was superior over administration of MMAE alone.

Example 11

In Vivo Efficacy Validation

Figure 13:
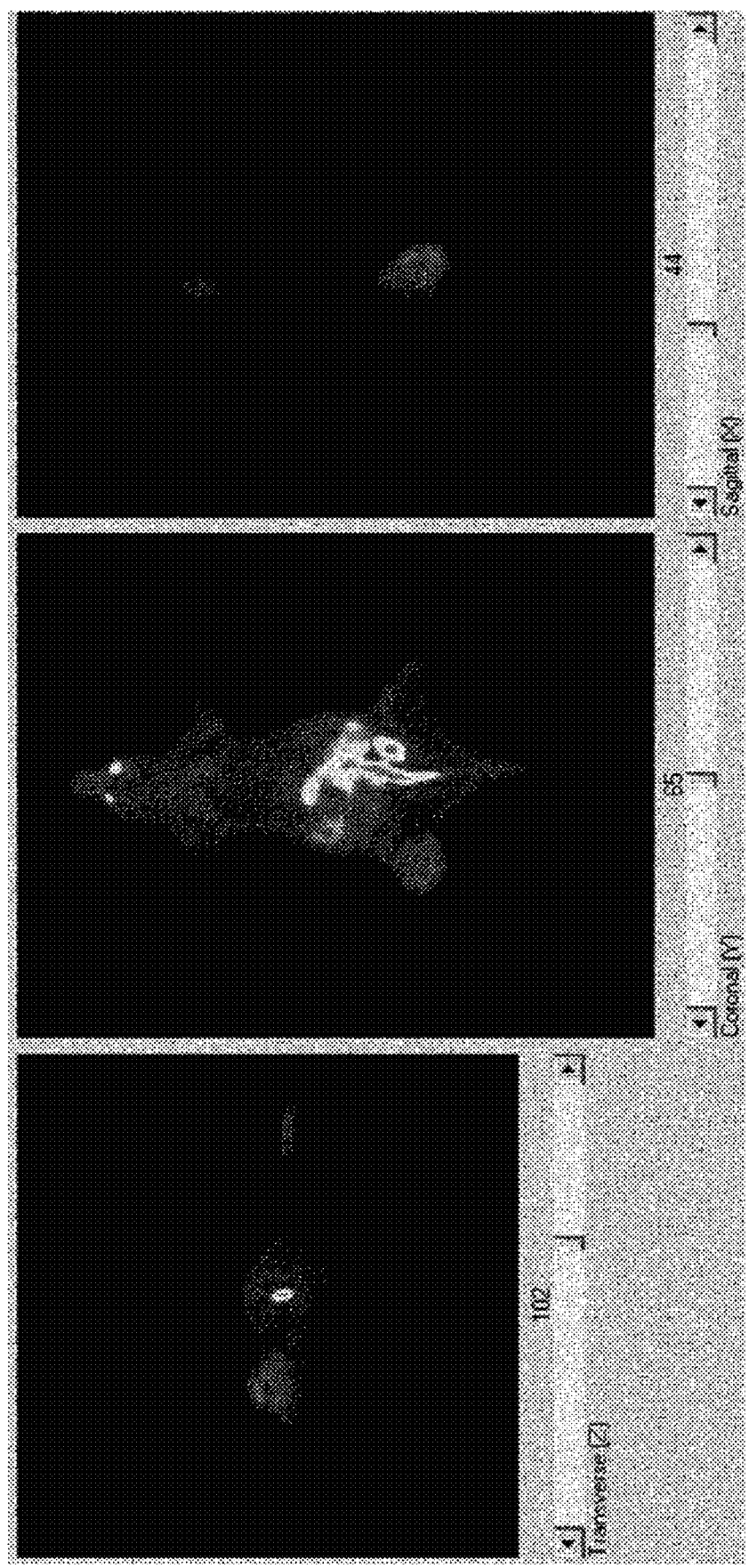
FIG. 13 illustrates FDG PET images obtained before treatment of Mv4-11 AML cell line-injected mice (a tumor with FDG intake in the left thigh region is observed).
Figure 14:
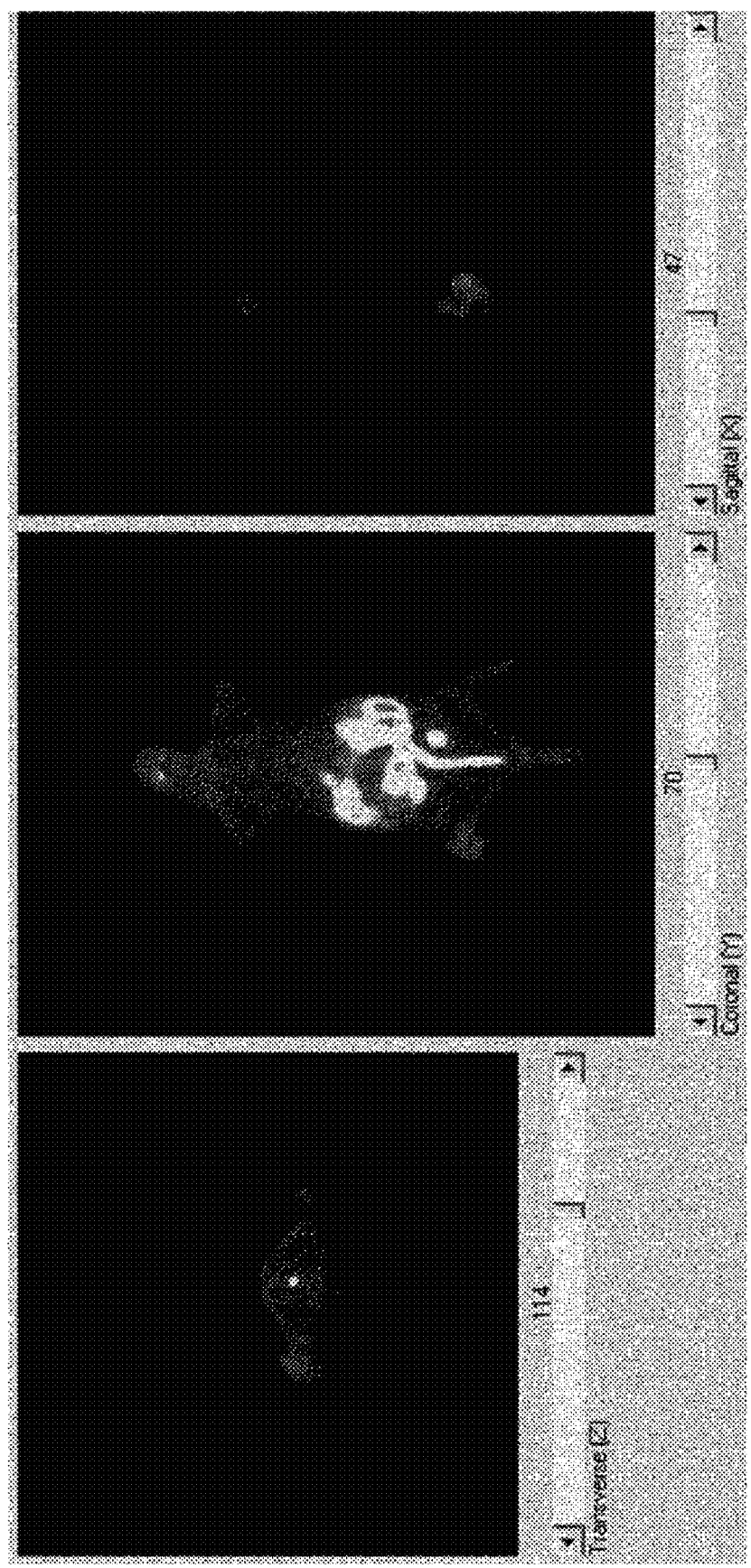
FIG. 14 illustrates FDG PET images obtained 30 days after treatment of Mv4-11 AML cell line-injected mice with citravin-(GLFG-MC-S-C6)-$T_3$-AS1411 (a decrease in FDG intake in the tumor is observed).

Validation of In Vivo Therapeutic Efficacy of citravin-(GLFG-MC-S-C6)-$T_3$-AS1411 on Mv4-11 AML Cell Line-Injected Mice To Mv4-11 AML cell line-injected mice, citravin-(GLFG-MC-S-C6)-$T_3$-AS1411 and MMAE, respectively, were administered by IV injection for 30 days, followed by identifying tumor sizes through PET images. Mv4-11 AML cells in a number of 6.1×10$^6$ cells/ml were injected subcutaneously in the right thigh of each nude mouse. The tumor size was measured in 3 to 4 weeks after the injection and, when a diameter of the tumor reached 0.8 cm, microPET images were captured before treatment. For PET images, F-18 FDG 0.2 mCi was i.p. injected and then the images were captured (Siemens Inveon). After detection of FDG intake in the tumor from the images, citravin-(GLFG-MC-S-C6)-$T_3$-AS1411 was i.v. injected in an experimental group of 5 mice 4 times by 5 day intervals (7.5 mg/kg, 0.5 mg/kg of MMAE). After 30 days from the start of treatment, microPET images were captured by the same method as used before treatment (FIG. 13 and FIG. 14).

Example 12

Figure 15:
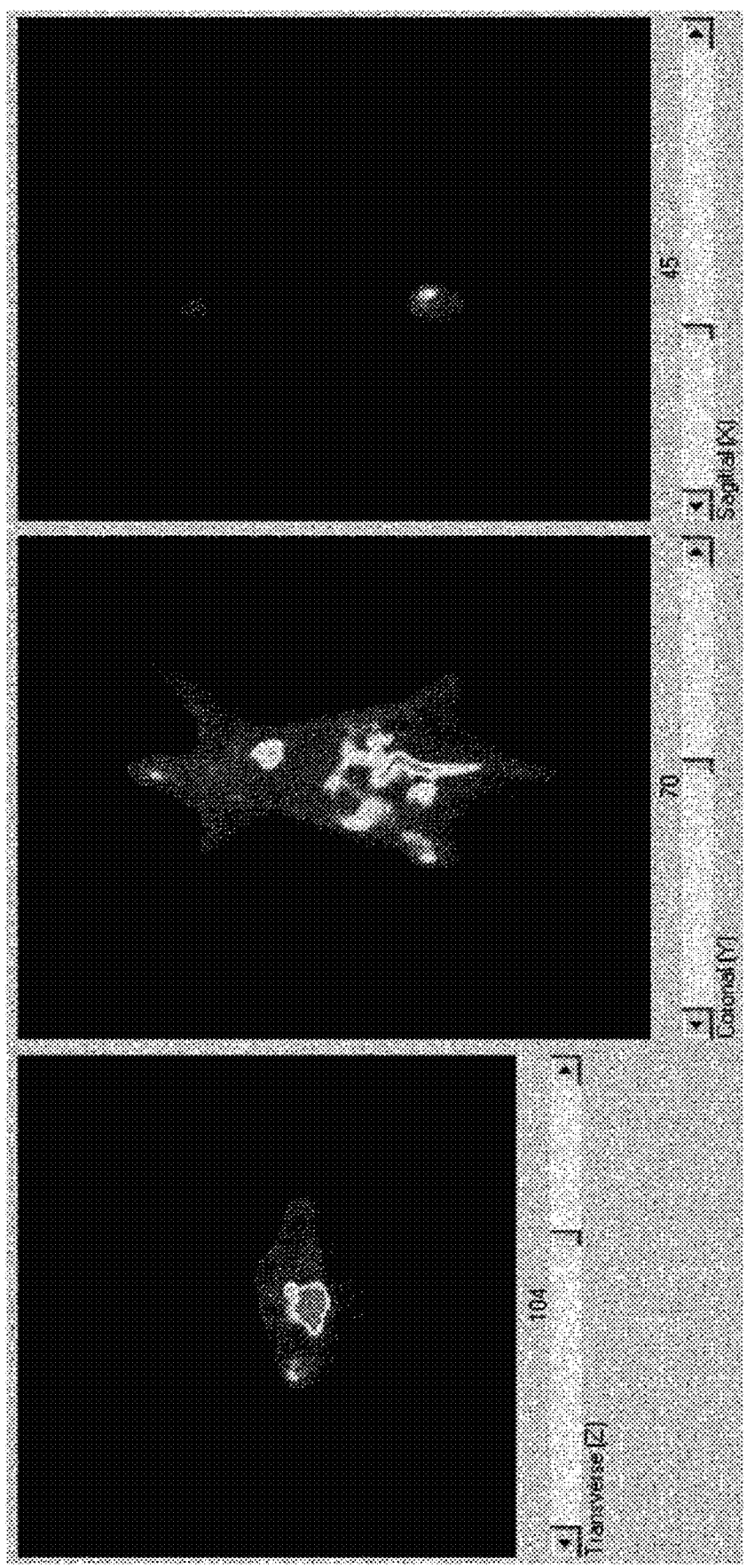
FIG. 15 illustrates FDG PET images obtained before treatment of Mv4-11 AML cell line-injected mice (a tumor with FDG intake in the left thigh region is observed).
Figure 16:
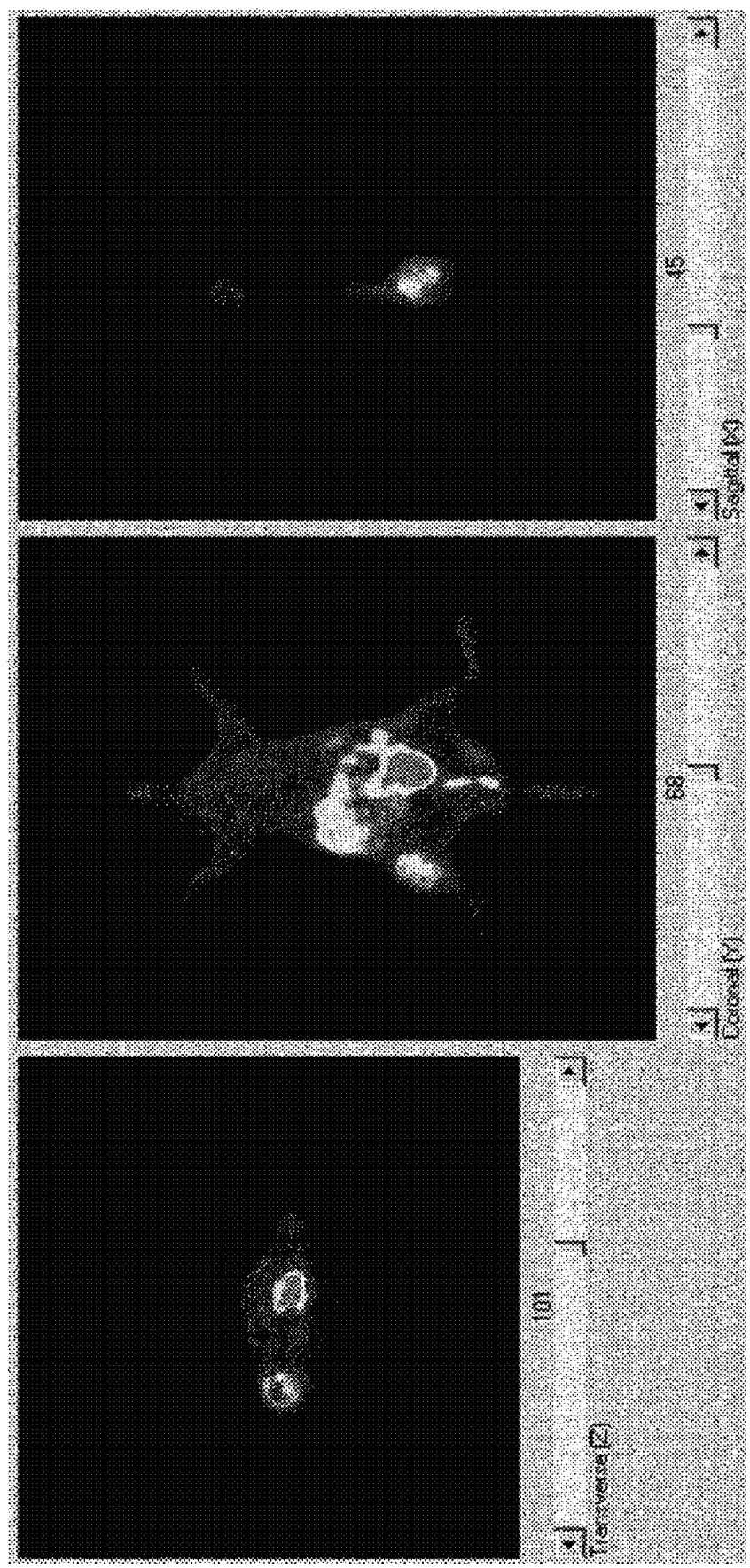
FIG. 16 illustrates FDG PET images obtained 30 days after treatment of Mv4-11 AML cell line-injected mice with MMAE (an increase in FDG intake in the tumor is observed).

Validation of In Vivo Therapeutic Efficacy of MMAE on Mv4-11 AML Cell Line-Injected Mice To Mv4-11 AML cell line-injected mice, MMAE was administered by IV injection for 30 days, followed by observation of PET images. Mv4-11 AML cells in the number of 6.1×10$^6$ cells/ml were injected subcutaneously in the right thigh of each nude mouse. The tumor size was measured in 3 to 4 weeks after the injection and, when a diameter of the tumor reached 0.8 cm, microPET images were captured before treatment. For PET images, F-18 FDG 0.2 mCi was i.p. injected and then the images were captured (Siemens Inveon). After detection of FDG intake in the tumor from the images before treatment, MMAE was i.v. injected in an experimental group of 5 mice 4 times by 5 day intervals (0.5 mg/kg). After 30 days from the start of treatment, microPET images were captured by the same method as used before treatment. Compared to before MMAE treatment, it was identified from FDG PET images that FDG intake in the tumor was increased even after treatment (FIG. 15 and FIG. 16).

Example 13

In Vitro Efficacy Validation

Figure 17:
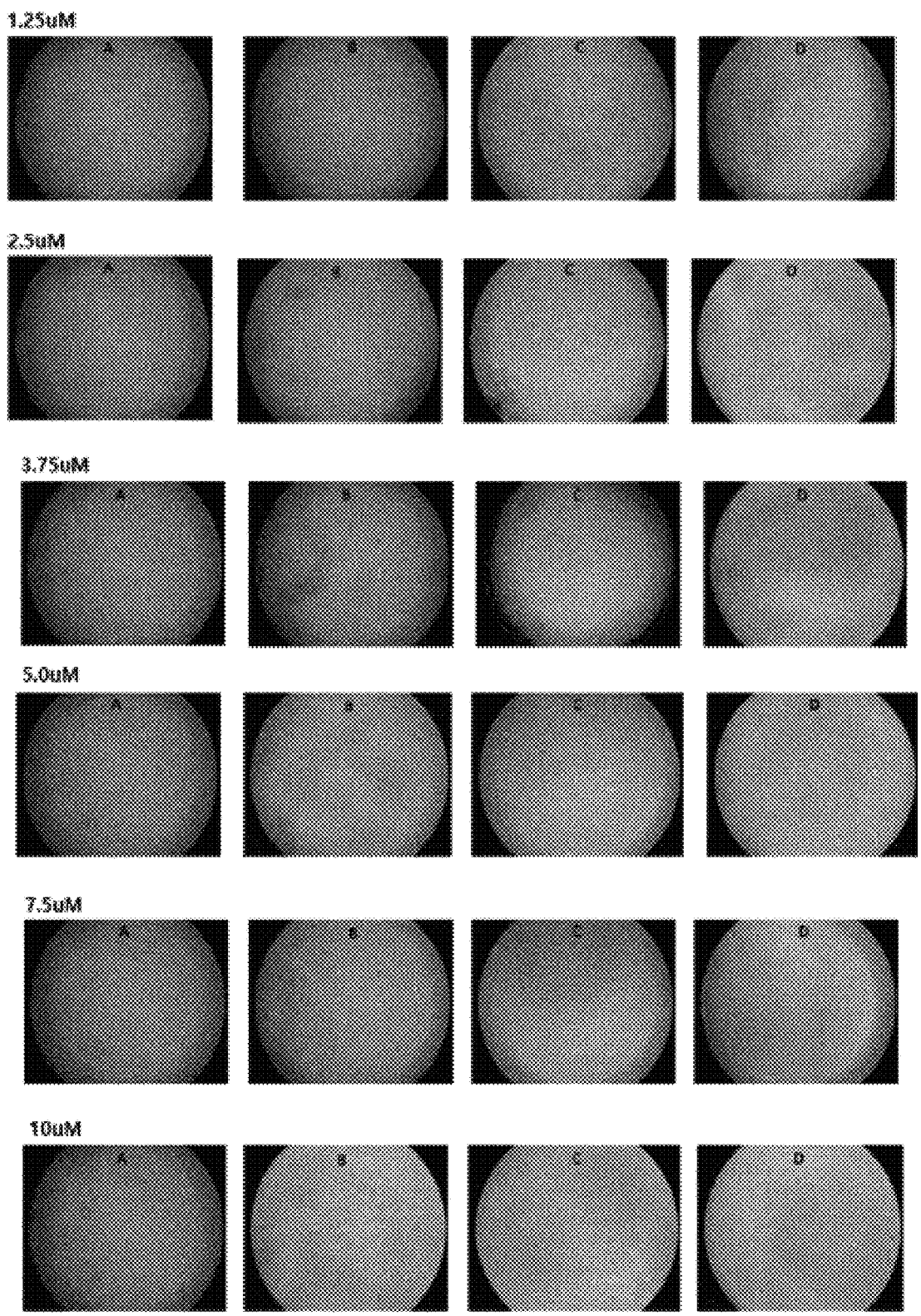
FIG. 17 illustrates A549 cell viability in each of MMAE-(PAB-Cit-Val-MC-S-C6)-$T_3$-AS1411, 12 or 13-(MMAE-PAB-Cit-Val-MC-S-C6)-AS1411 and 12,13-(MMAE-PAB-Cit-Val-MC-S-C6)$_2$-AS1411 at different concentrations.

MTT Assay of MMAE-(PAB-Cit-Val-MC-S-C6)-$T_3$-AS1411, or 13-(MMAE-PAB-Cit-Val-MC-S-C6)-AS1411 and 12,13-(MMAE-PAB-Cit-Val-MC-S-C6)$_2$-AS1411 to A549 Cell Lines With regard to A549 cell line as a lung cancer cell line over-expressing a nucleoline protein, cell inhibition efficacies of MMAE-(PAB-Cit-Val-MC-S-C6)-$T_3$-AS1411, 12 or 13-(MMAE-PAB-Cit-Val-MC-S-C6)-AS1411 and 12,13-(MMAE-PAB-Cit-Val-MC-S-C6)$_2$-AS1411 were verified in vitro by MTT assay. When comparing cell viability and cell proliferation of the cells through MTT assay of MMAE-(PAB-Cit-Val-MC-S-C6)-$T_3$-AS1411, 12 or 13-(MMAE-PAB-Cit-Val-MC-S-C6)-AS1411 and 12,13-(MMAE-PAB-Cit-Val-MC-S-C6)$_2$-AS1411, respectively, it was demonstrated that 12,13-(MMAE-PAB-Cit-Val-MC-S-C6)$_2$-AS1411 has superior efficacy over of MMAE-(PAB-Cit-Val-MC-S-C6)-$T_3$-AS1411. A549 cells (ATCC, IMDM+ 10% FBS) were seeded on a 96-well plate in a cell number of 2.5 to 5×10$^5$ cells/well, which was determined by a cell test method to determine an appropriate cell concentration, followed by growing for 1 day. After heating each of MMAE-(PAB-Cit-Val-MC-S-C6)-$T_3$-AS1411, 12 or 13-(MMAE-PAB-Cit-Val-MC-S-C6)-AS1411 and 12,13-(MMAE-PAB-Cit-Val-MC-S-C6)$_2$-AS1411 at 95° C. for 5 minutes, the heated product was gradually cooled at room temperature and directly treated on each well at different concentrations. After incubating the treated A549 cells in 5% $CO_2$ incubator for 72 hours, the incubated product was treated with 20 μL of a reagent solution for MTT assay (Cell Proliferation kit II, Roche) and incubated for different periods of time (10 min, 30 min, 1 hr). Thereafter, the final product was subjected to measurement of absorbance at 490 nm by an ELISA reader (FIG. 17). In FIGS. 17, A, B, C and D are as follows.

TABLE 1

| | MMAE-Linker-Aptamer conjugate |
|---|---|
| A | MMAE-(PAB-Cit-Val-MC-S-C6)-$T_3$-CRO |
| B | MMAE-(PAB-Cit-Val-MC-S-C6)-$T_3$-AS1411 |
| C | 12 or 13-(MMAE-PAB-Cit-Val-MC-S-C6)-AS1411 |
| D | 12,13-(MMAE-PAB-Cit-Val-MC-S-C6)$_2$-AS1411 |

Figure 18:
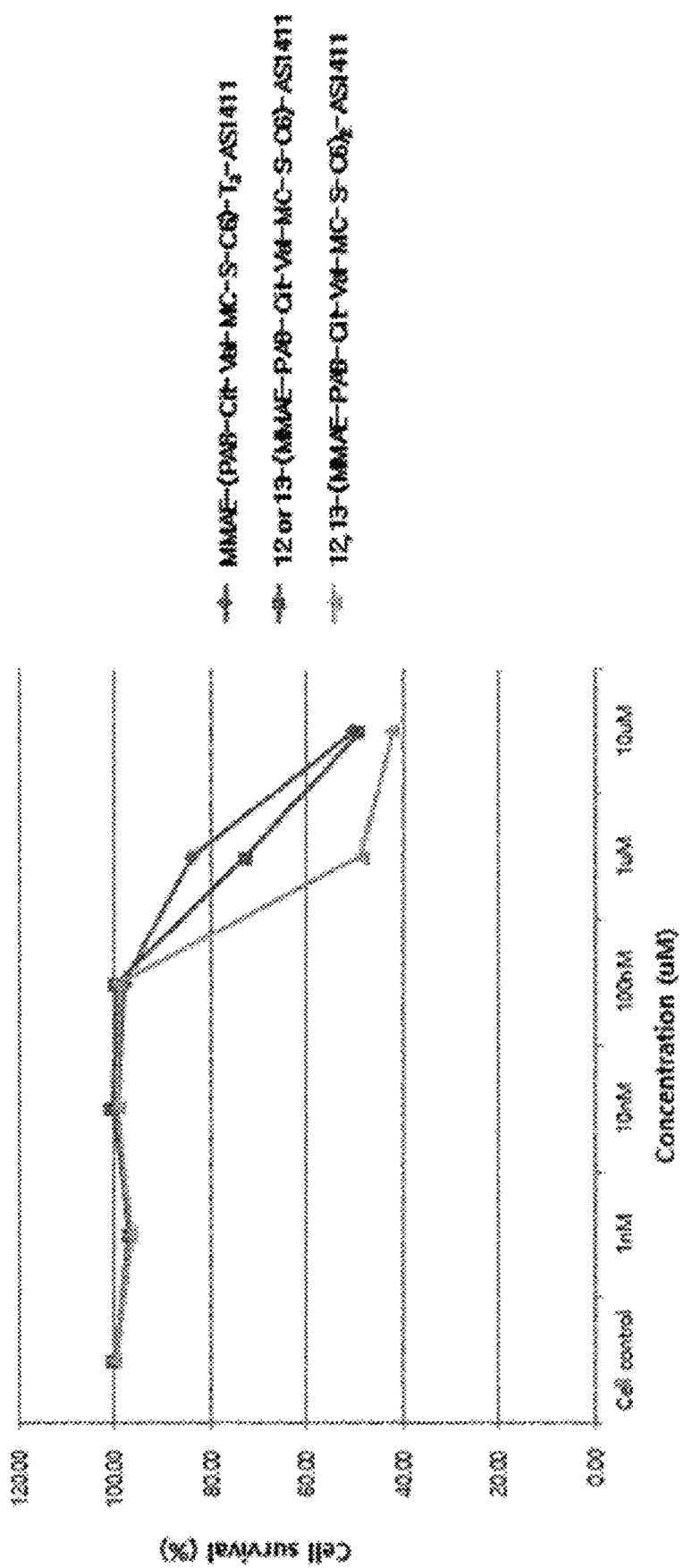
FIG. 18 illustrates MTT assay results of MMAE-(PAB-Cit-Val-MC-S-C6)-$T_3$-AS1411, 12 or 13-(MMAE-PAB-Cit-Val-MC-S-C6)-AS1411 and 12,13-(MMAE-PAB-Cit-Val-MC-S-C6)$_2$-AS1411 to A549 cell lines.

FIG. 18 illustrates MTT assay results of MMAE-(PAB-Cit-Val-MC-S-C6)-$T_3$-AS1411, 12 or 13-(MMAE-PAB-Cit-Val-MC-S-C6)-AS1411 and 12,13-(MMAE-PAB-Cit-Val-MC-S-C6)$_2$-AS1411 to the A549 cell lines.

The AS1411-drug conjugate of the present invention can be usefully used as a cancer targeted therapeutic agent.

The invention claimed is:

1. A cancer targeted therapeutic agent, comprising:

a drug-linker-modified AS1411 structure, wherein the drug is selected from the group consisting of monomethyl auristatin E (MMAE), monomethyl auristatin F (MMAF), cytarabine, gemcitabine, maytansine, DM1 represented by Formula 1, DM4 represented by Formula 2, calicheamicin, acylated calicheamicin, doxorubicin, duocarmycin, pyrrolobenzodiazepine (PBD), SN-38 represented by Formula 3, or α-ammantin;

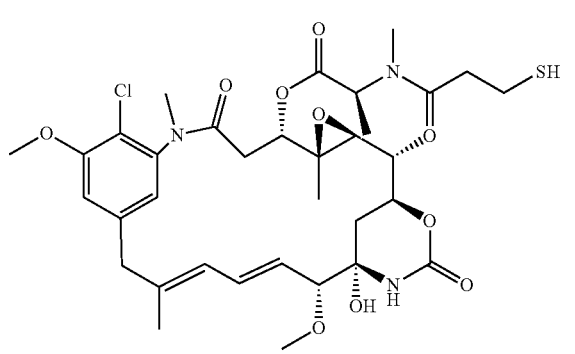

Formula 1

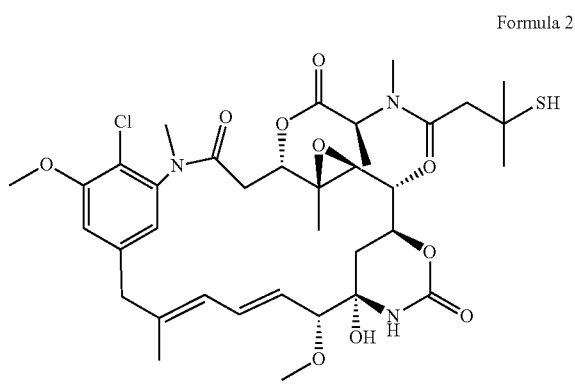

Formula 2

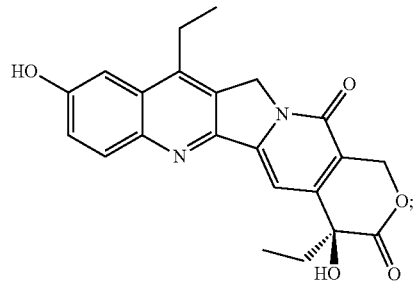

Formula 3 and the linker is X-Y, wherein Y is selected from the group consisting of: maleimidocaproyl-valine-citrulline-p-aminobenzoyloxycarbonyl (MC-Val-Cit-PAB), maleimidocaproyl-glycine-phenylalanine-leucine-glycine (MG-Gly-Phe-Leu-Gly), hydrazone, disulfide, thioether, valine-citrulline, N-maleimdomethylcyclohexane-1-carboxylate (MCC), maleimidocaproyl, mercaptoacetamidocaproly, N-succinimidyl 4-(2-pyridyldithio)pentanoate (SPP), succinimidyl 4-(N-maleimidomethyl)cyclohexane-1-carboxylate (SMCC), and N-succinimidyl 4-(2-pyridylthio)pentanoate (SPDB), X is selected from the group consisting of: 5'-thiol-modifier C6, thiol-modifier C6 S—S, dithiolserinol, PC amino-modifier, 5'-amino-modifier C3, 5'-amino-modifier C6, 5'-amino-modifier C12, amino-modifier C2 dT, amino-modifier C6 dT, and S-Bz-thiol-modifier C6-dT, wherein X is linked to the modified AS1411 at a nucleotide residue of a 12 or 13 position or nucleotide residues of both 12 and 13 positions of the modified AS1411, and Y is bound to the drug; and the modified AS1411 has the sequence of SEQ ID NO: 1 with a modification that at least one of the nucleotide residue of the 12 and 13 position of the SEQ ID NO: 1 is substituted with uracil.

2. The cancer targeted therapeutic agent of claim 1, wherein the drug is monomethyl auristatin E (MMAE) or cytarabine.

3. The cancer targeted therapeutic agent of claim 1, wherein Y is maleimidocaproyl-valine-citrulline-p-aminobenzoyloxycarbonyl (MC-Val-Cit-PAB) or maleimidocaproyl-glycine-phenylalanine-leucine-glycine (MC-Gly-Phe-Leu-Gly), X is 5'-thiol-modifier C6, and Y has a side of maleimidocaproyl bound to the drug and the other side bound to X.

4. The cancer targeted therapeutic agent of claim 1, wherein the modified AS1411 has the sequence of SEQ ID NO: 9.

\* \* \* \* \*

SEQUENCE LISTING

```
<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: as1411 aptamer

<400> SEQUENCE: 1
ggtggtggtg gttgtggtgg tggtgg                                          26

<210> SEQ ID NO 2
<211> LENGTH: 29
<212> TYPE: DNA
<213> ORGANISM: Artificial Sequence
<220> FEATURE:
<223> OTHER INFORMATION: t3-as1411 aptamer

<400> SEQUENCE: 2
tttggtggtg gtggttgtgg tggtggtgg                                       29

<210> SEQ ID NO 3
<211> LENGTH: 29
<212> TYPE: DNA
<213> ORGANISM: Artificial Sequence
<220> FEATURE:
<223> OTHER INFORMATION: t3-CRO

<400> SEQUENCE: 3
tttcctcctc ctccttctcc tcctcctcc                                       29
```

<210> SEQ ID NO 4
<211> LENGTH: 12
<212> TYPE: DNA
<213> ORGANISM: Artificial Sequence
<220> FEATURE:
<223> OTHER INFORMATION: a sequence for syhthesizing AS1411-drug
      conjugate

<400> SEQUENCE: 4
ggtggtggtg gu                                                         12

<210> SEQ ID NO 5
<211> LENGTH: 14
<212> TYPE: DNA
<213> ORGANISM: Artificial Sequence
<220> FEATURE:
<223> OTHER INFORMATION: a sequence for syhthesizing AS1411-drug
      conjugate

<400> SEQUENCE: 5
ugtggtggtg gtgg                                                       14

<210> SEQ ID NO 6
<211> LENGTH: 13
<212> TYPE: DNA
<213> ORGANISM: Artificial Sequence
<220> FEATURE:
<223> OTHER INFORMATION: a sequence for syhthesizing AS1411-drug
      conjugate

<400> SEQUENCE: 6
gtggtggtgg tgg                                                        13

<210> SEQ ID NO 7
<211> LENGTH: 4
<212> TYPE: PRT
<213> ORGANISM: Artificial Sequence
<220> FEATURE:
<223> OTHER INFORMATION: a part of a linker for syhthesizing AS1411-drug
      conjugate

<400> SEQUENCE: 7

Gly Phe Leu Gly
1

<210> SEQ ID NO 8
<211> LENGTH: 4
<212> TYPE: PRT
<213> ORGANISM: Artificial Sequence
<220> FEATURE:
<223> OTHER INFORMATION: a part of a linker for syhthesizing AS1411-drug
      conjugate

```
<400> SEQUENCE: 8

Gly Leu Phe Gly
1

<210> SEQ ID NO 9
<211> LENGTH: 26
<212> TYPE: DNA
<213> ORGANISM: Artificial Sequence
<220> FEATURE:
<223> OTHER INFORMATION: modified as1411 aptamer

<400> SEQUENCE: 9
ggtggtggtg guugtggtgg tggtgg                                          26
```